United States Patent
Podhajcer et al.

(10) Patent No.: US 9,056,133 B2
(45) Date of Patent: Jun. 16, 2015

(54) PHARMACEUTICAL KIT AND METHOD FOR TREATING CANCER

(75) Inventors: Osvaldo Podhajcer, Buenos Aires (AR); Manuel Gidekel, Santiago (CL); Eduardo Cafferata, Buenos Aires (AR); Helga Weber, Pucon (CL)

(73) Assignee: CTI-S.A., Santiago (CL)

( * ) Notice: Subject to any disclaimer, the term of this patent is extended or adjusted under 35 U.S.C. 154(b) by 0 days.

(21) Appl. No.: 13/506,865

(22) Filed: May 21, 2012

(65) Prior Publication Data

US 2013/0084263 A1 Apr. 4, 2013

(51) Int. Cl.
*A61K 48/00* (2006.01)
*A61K 31/7068* (2006.01)
*A61K 38/46* (2006.01)
*A61K 35/761* (2015.01)

(52) U.S. Cl.
CPC ......... *A61K 48/0058* (2013.01); *A61K 31/7068* (2013.01); *A61K 38/465* (2013.01); *A61K 35/761* (2013.01)

(58) Field of Classification Search
None
See application file for complete search history.

(56) References Cited

U.S. PATENT DOCUMENTS 6,911,199 B2 * 6/2005 Vigne et al. .................. 424/93.2
8,398,968 B2 * 3/2013 Mayall ......................... 424/93.2

FOREIGN PATENT DOCUMENTS

CN 101358199 A * 2/2009
WO WO 2007127347 A2 * 11/2007

OTHER PUBLICATIONS

Tang et al. Oncol Rep 2011;25:963-70.*
Fridlender et al. Mol Ther Nov. 2010;18:1947-59.*

* cited by examiner

*Primary Examiner* — Janice Li
(74) *Attorney, Agent, or Firm* — John Dodds

(57) ABSTRACT

This invention is related to the field of cancer treatment, more specifically to gene therapy in combination with a suitable chemotherapeutic agent. The present invention is related to a new oncolytic virus, which is able to inhibit the growth of malignant tumors or is a treatment of hyperproliferative mammalian cells, or is a treatment of cancer. The oncolytic virus works in combination with a suitable chemotherapeutic agent. More specifically, the present invention provides a pharmaceutical kit comprising an oncolytic adenovirus and a chemotherapeutic agent, and a method for the treatment of cancer.

17 Claims, 19 Drawing Sheets

FIGURE 1 cgcgtggggtgtctaacgcagaccgtacagccagctgggtttagcaaacttccgggagccagttggagcctctctc ccaat/Putative Enhancer cccatccctagcggtgatcccaggtgacgacatgccgcgggggtcctgcggaggccaccctagggcgttgctg putative p53 ctgcctttgggagtgtggagctccaaaccatgtcgcgagaggcggatttgggaggccgggatcctcgcgccagg

Putative E2F gggatgtgcgagggtgt gggataaatcttaattcctccggcccacccaaagcctggaaatccagcctccgcgcct cttgccctgcgggccccgcctcagtcccgccctcatctaacccgctaccccattggtggcgtccggcggcgcgg

SP1   SP1   NF-Y ctgctgttattttcgaatatataaggaggtggaagtggcagctgcaactagaggcttccctggctggtgcctgagcc TATA   Putative Inr cggcga

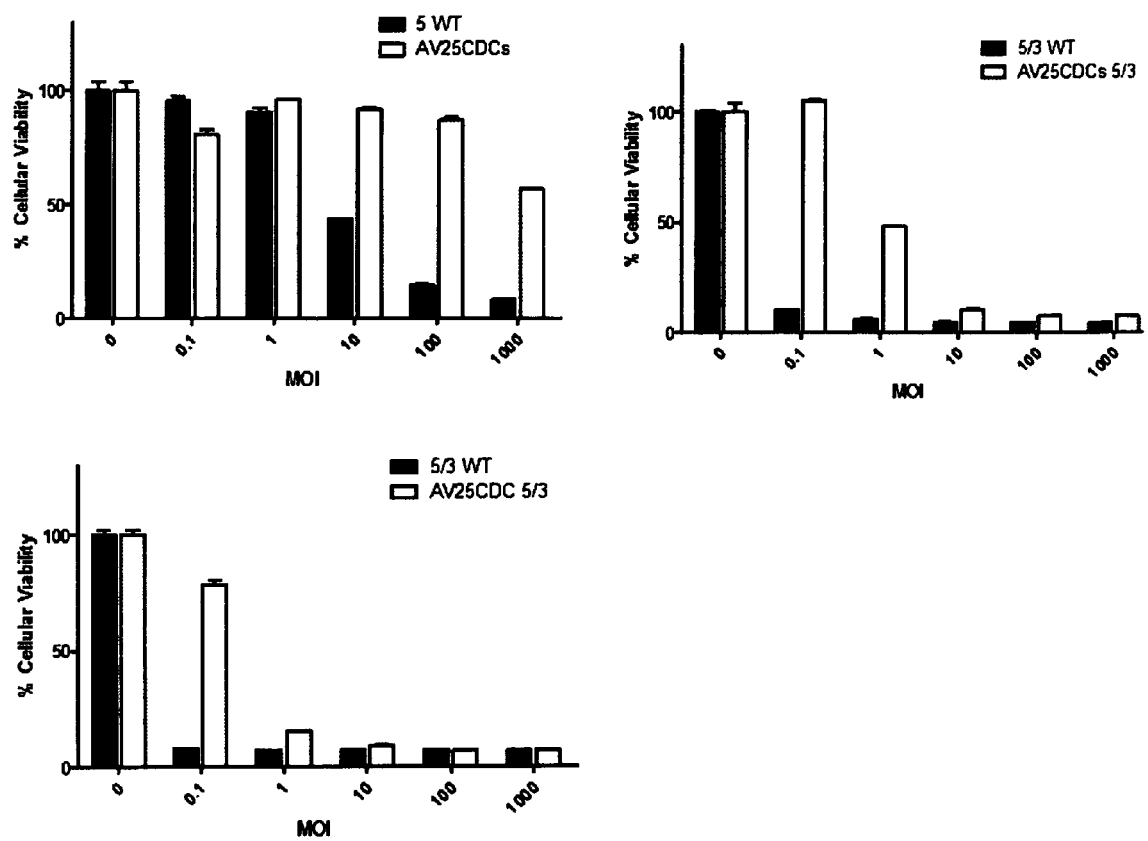

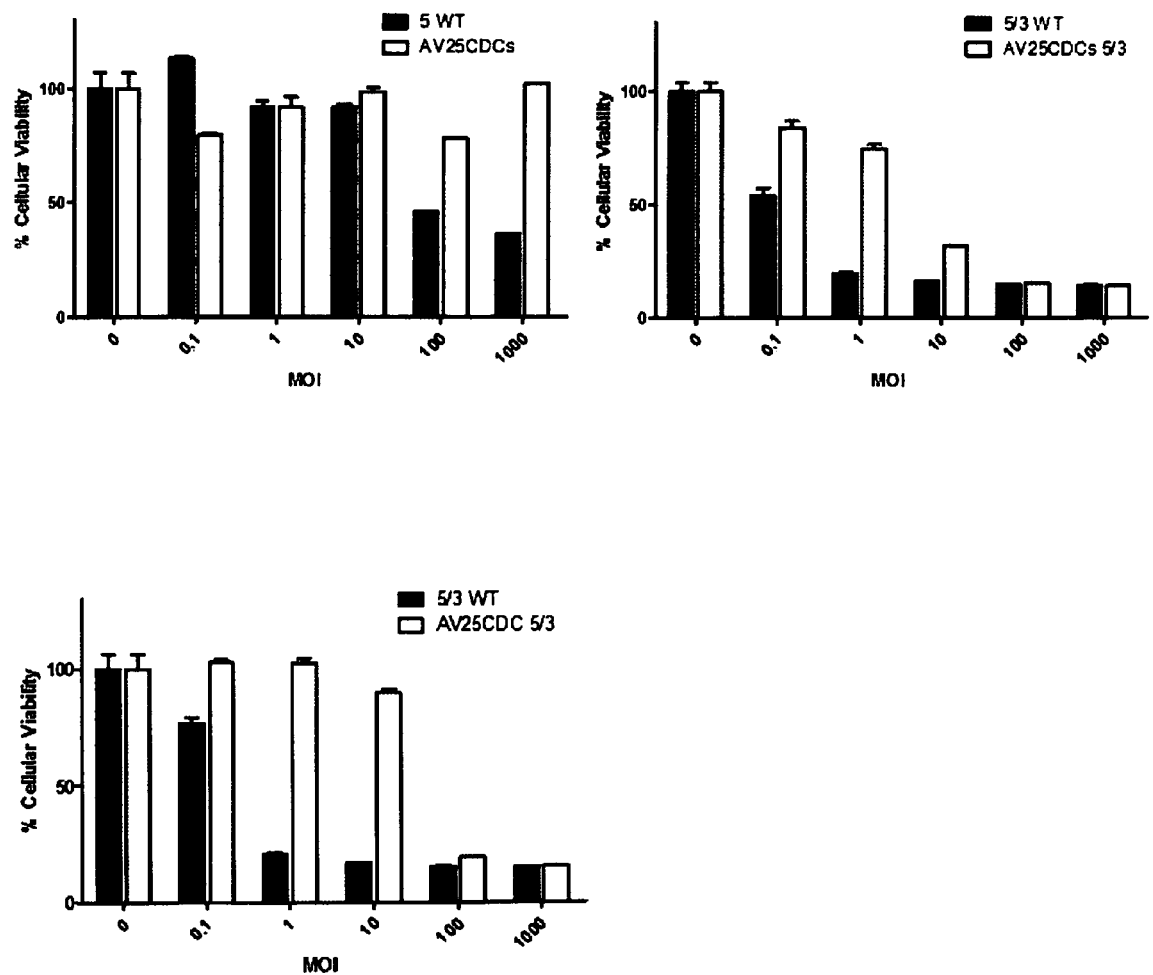
Figure 4. (b) HS766T

Figure 4 (c) Mia Paca 2
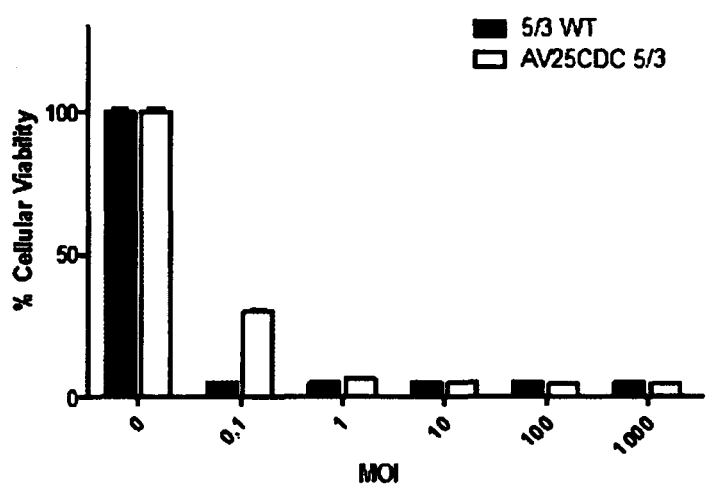

Figure 4. (d) SW1990
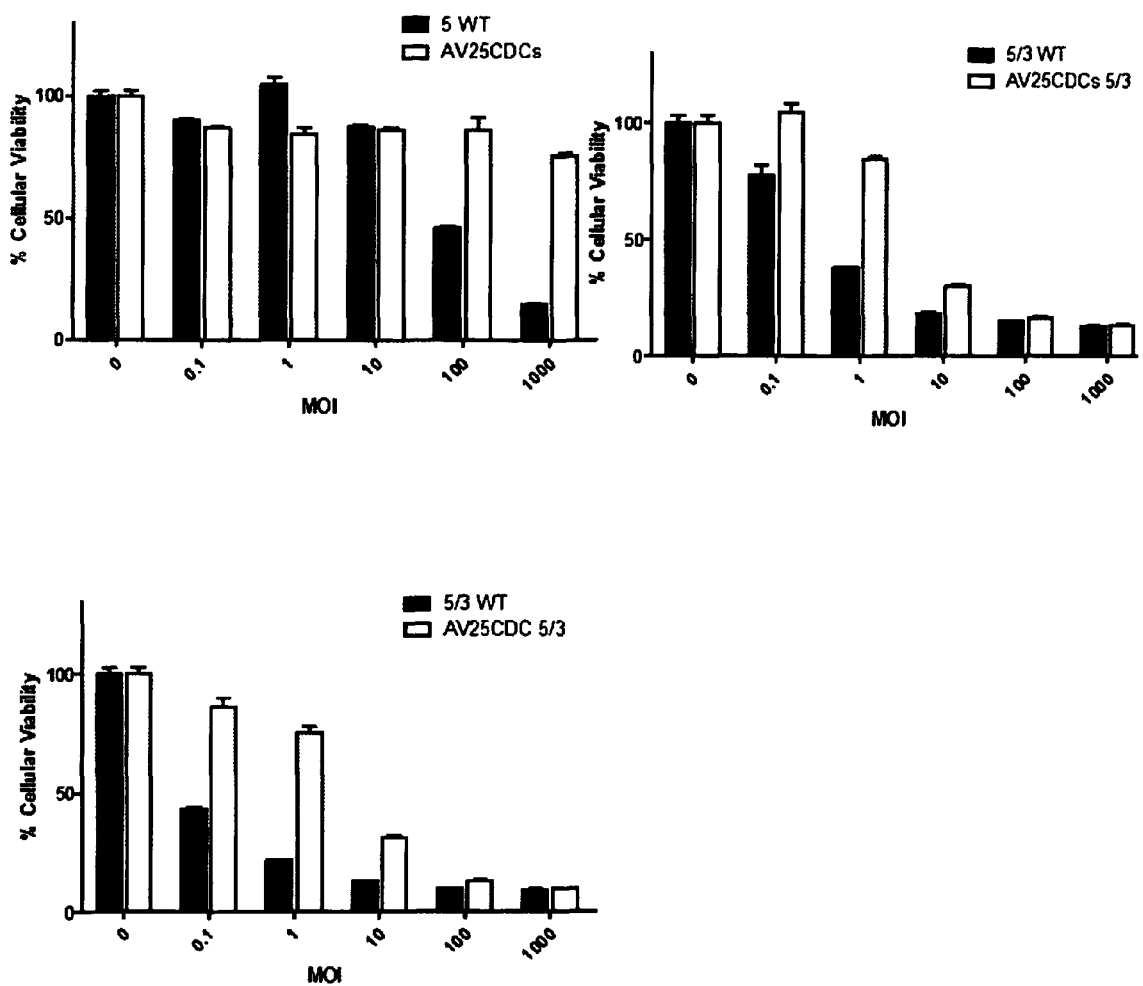

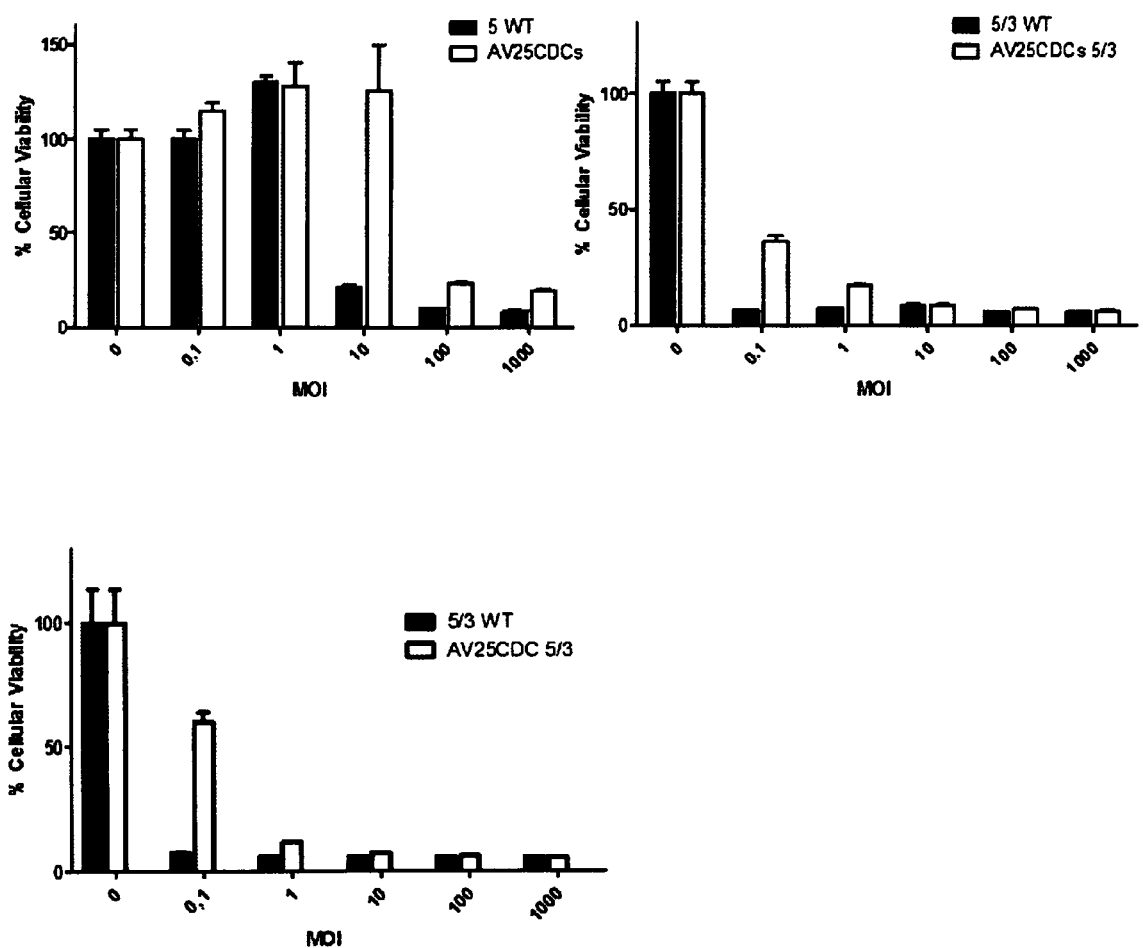
Figure 5. (a) HT29

Figure 5. (b) LoVo
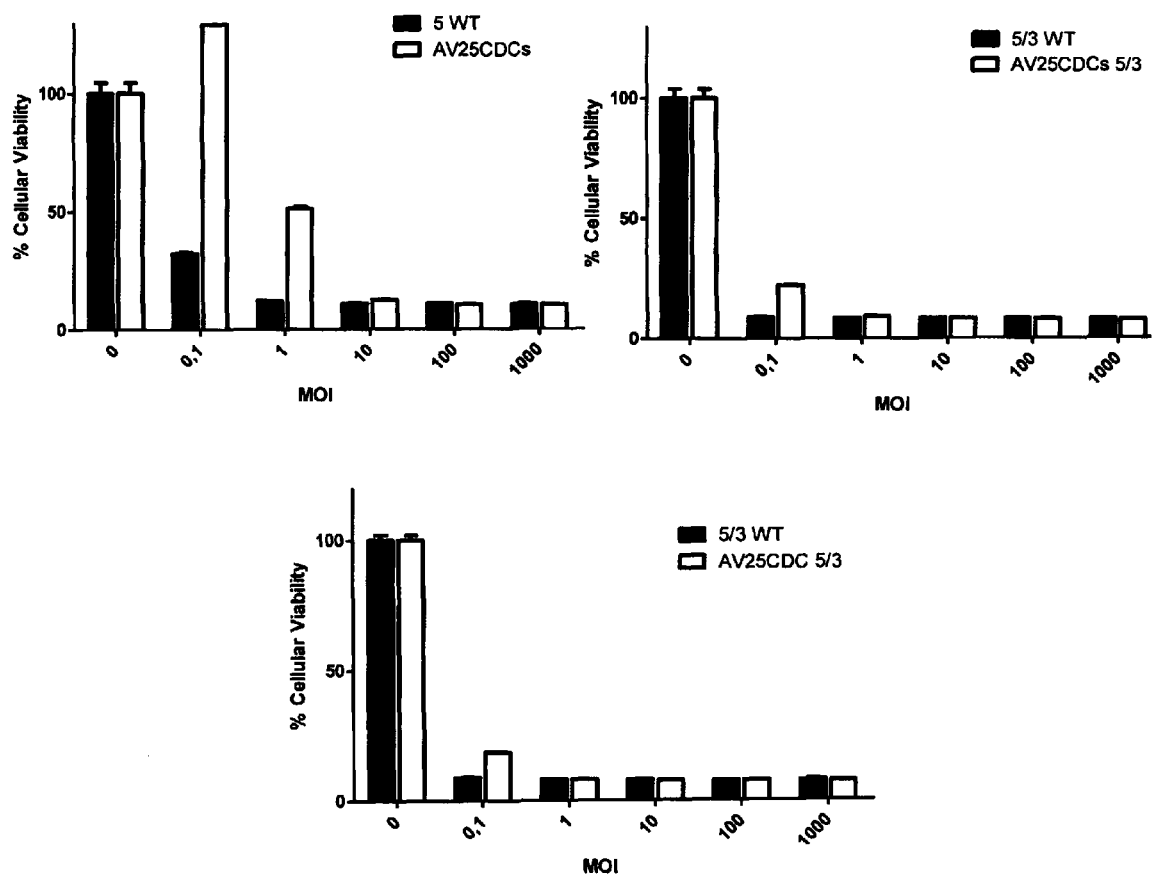

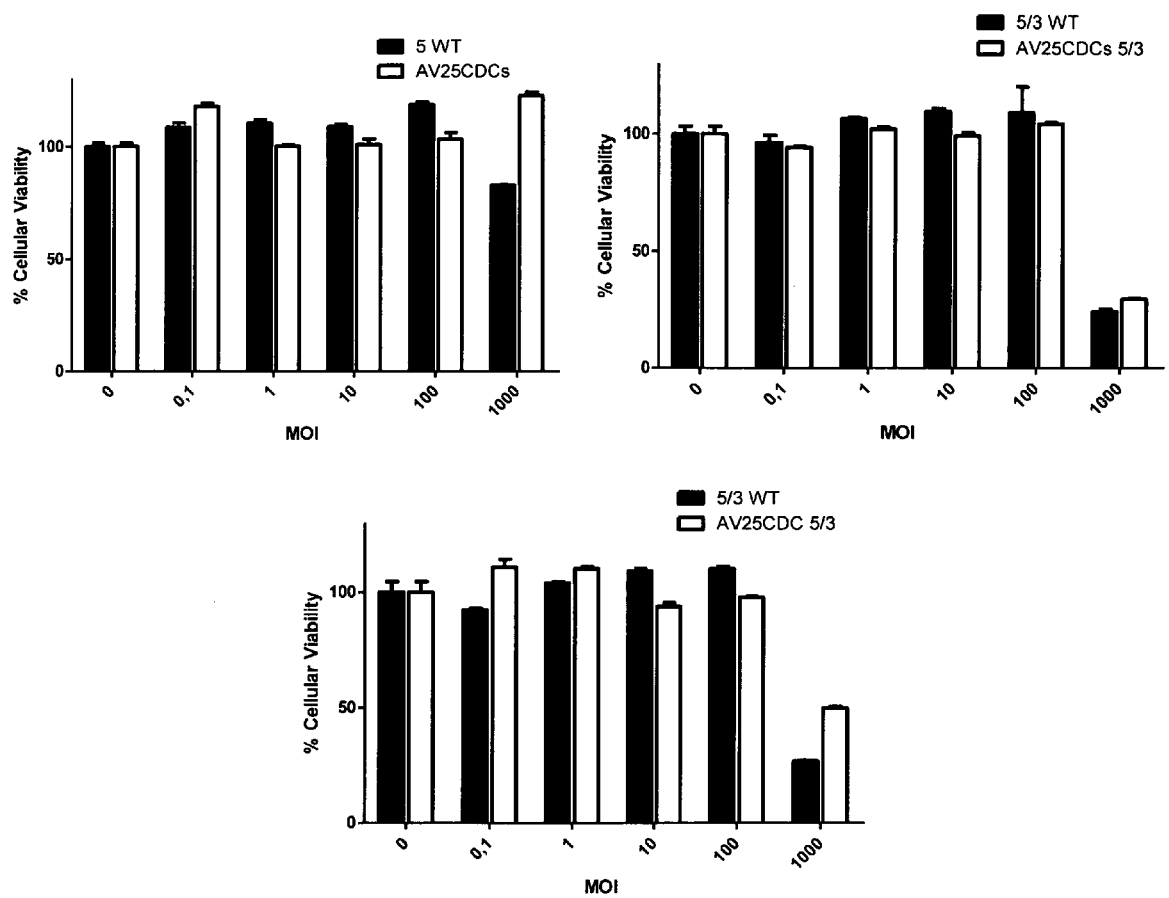
Figure 6. (a) CCD1140sk

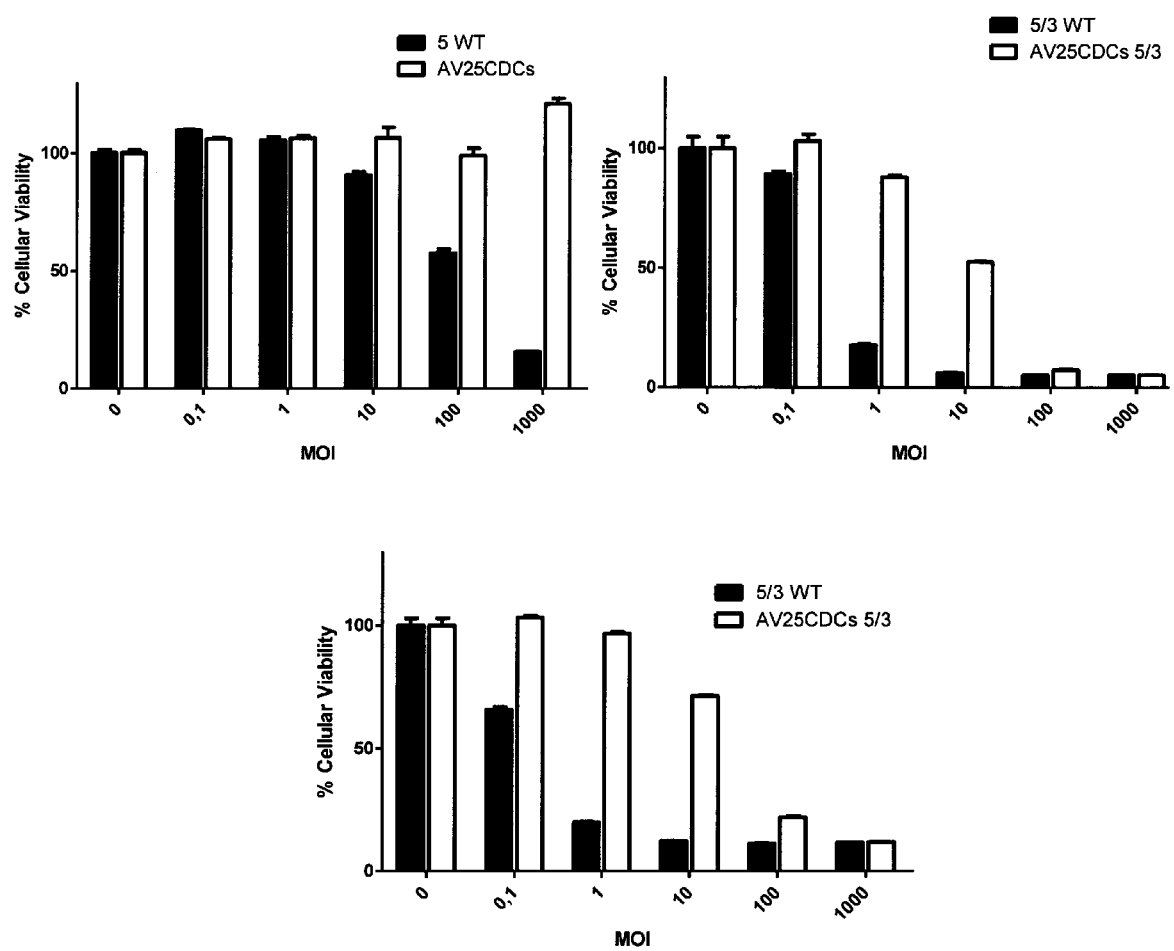

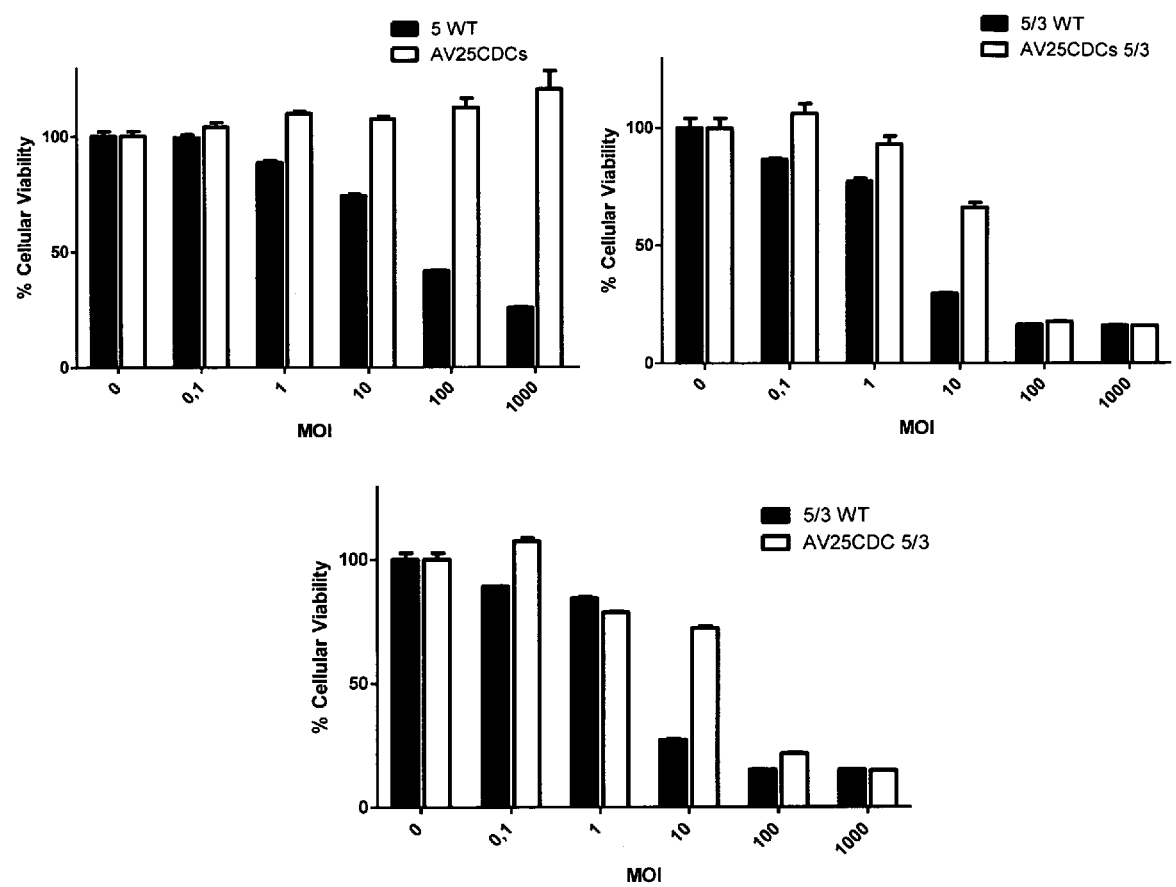
Figure 6. (c) WI38

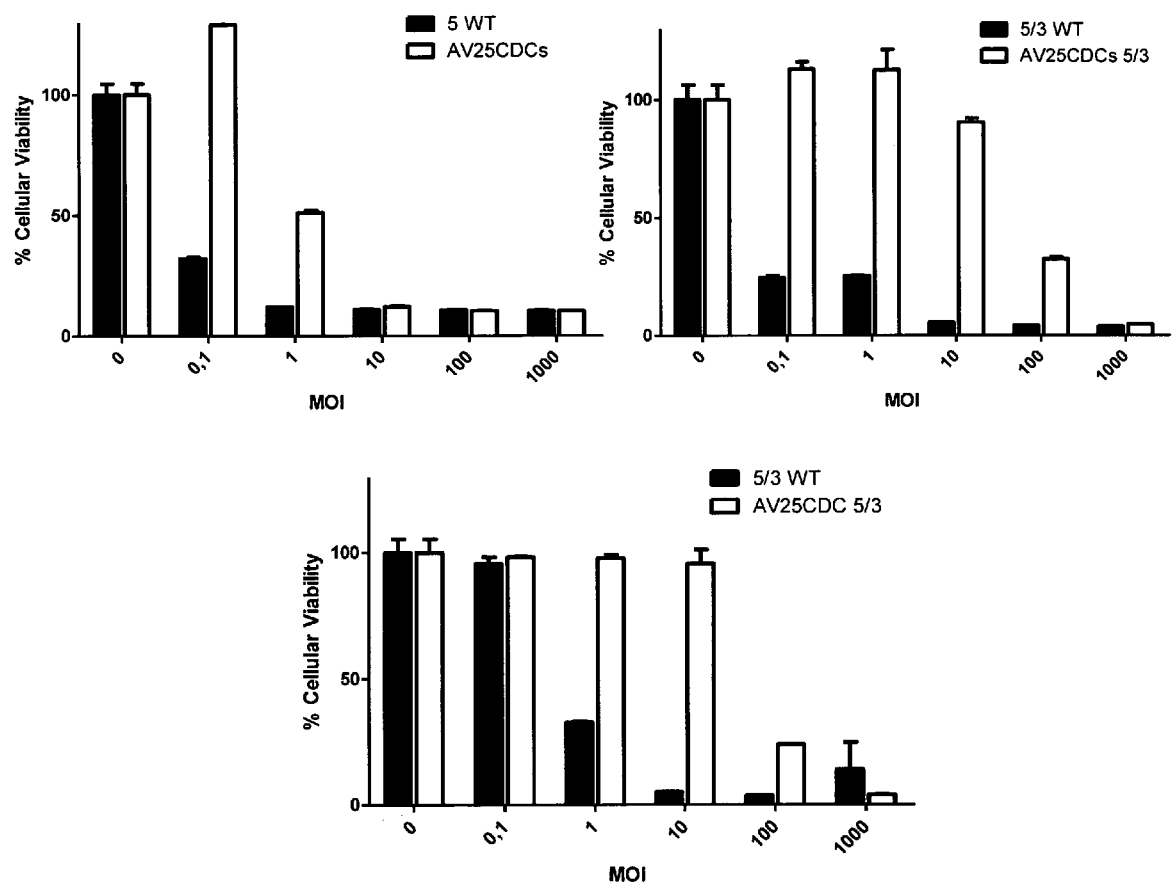
Figure 6. (d) HACAT

Figure 9
A
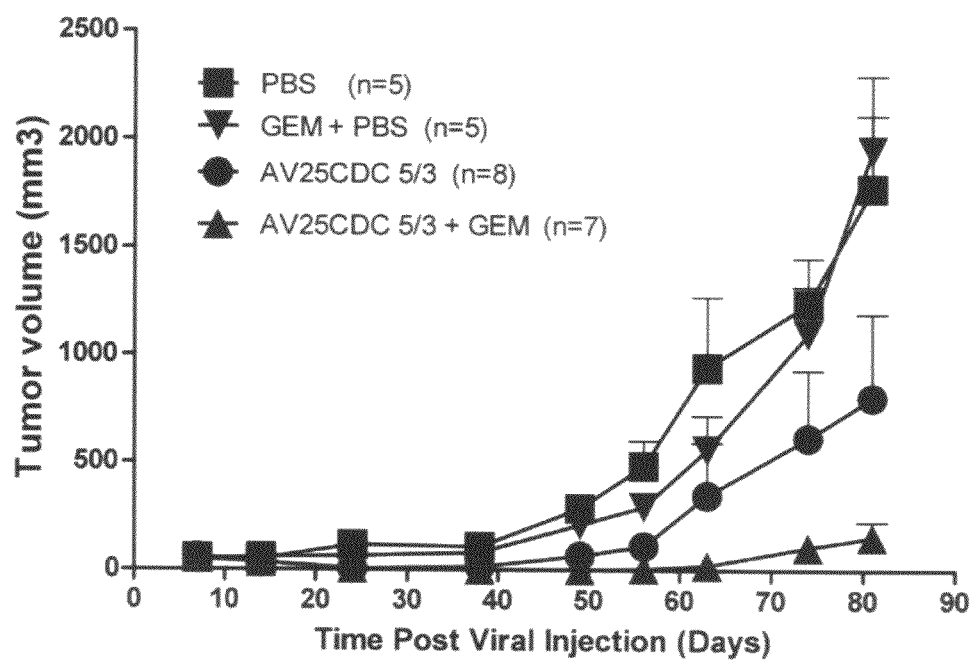
B
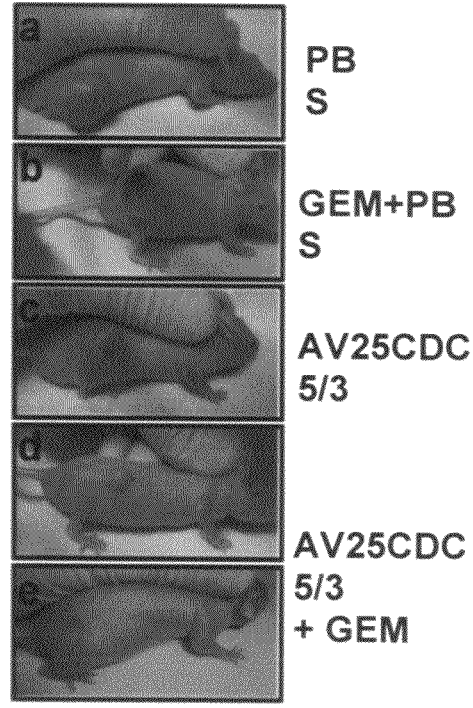

Figure 11:
A
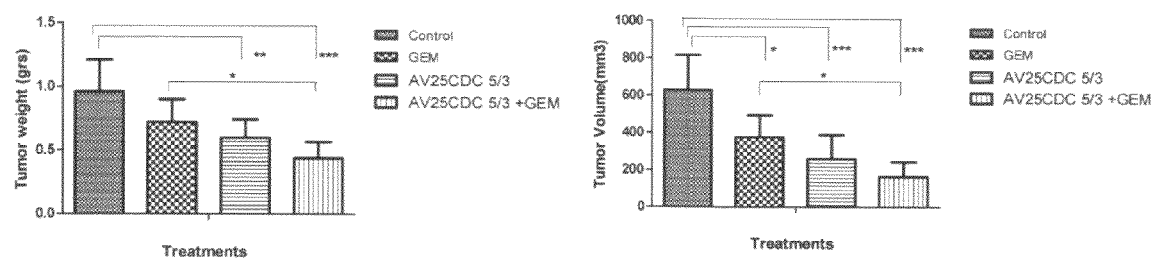
B
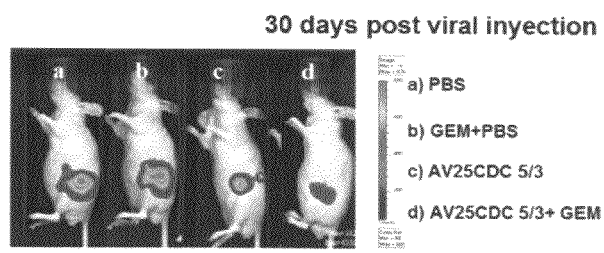
C
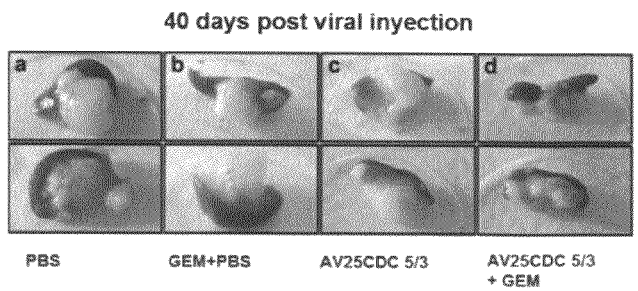

PHARMACEUTICAL KIT AND METHOD FOR TREATING CANCER

FIELD OF THE INVENTION

This invention is related to the field of cancer treatment, more specifically to gene therapy in combination with a suitable chemotherapeutic agent. The present invention is related to a new oncolytic virus, which is able to inhibit the growth of malignant tumors or is a treatment of hyperproliferative mammalian cells, or is a treatment of cancer. The oncolytic virus works in combination with a suitable chemotherapeutic agent. More specifically, the present invention provides a pharmaceutical kit comprising an oncolytic adenovirus and a chemotherapeutic agent, and a method for the treatment of cancer.

BACKGROUND OF THE INVENTION

Deregulation of the control of cell cycle is an important event in malignant transformation of tumoral cells and is a common characteristic to all types of cancer, where commonly is observed an alteration in genes controlling the cell cycle as well as proliferation.

In cell cycle control, there are 2 checkpoints which are critical: transition between phases G1-S and transition between phases G2-M. The principal components of the machinery of the cell cycle are cyclins and its correspondent ciclyn dependent kinases (CDK). These complexes CDK/cyclin are activated and inactivated sequentially, thus regulating the different phases of the cell cycle.

CDK/cyclins are subject to various mechanisms of control, including association with inhibitory proteins, such as p15lnk4b/p16lnk4a or p21Waf1/p27Kip1, activating phosphorylation on Thr160/161, activating CDK and inhibitory phosphorylation on Th14 and Tyr15 by Wee1 and Myt1 kinases.

Another control mechanism is exerted by CDC25 phosphatases, which are key in the control of the cell cycle in eukaryote cells, in normal conditions as well as in response to cell damage, and whose over expression is associated to a wide variety of cancer.

The physiological substrate of CDC25 phosphatases are CDKs. The complex CDK/cyclin is maintained inactive by phosphorylation of the minor lobule of CDK subunit, and in normal conditions, during cell division, a member of this class of phosphatases dephosphorylates CDK, thus allowing progression of the cell cycle.

Three isoforms of CDC25 phosphatases have been identified in mammals: Cdc25A, Cdc25B, and Cdc25C.

Human Cdc25 proteins have between 423 and 566 aminoacids, with a conserved catalytic domain compared to the regulatory regions, which are more diverse and subject to splicing events. These variability generates in humans 3 variants for Cdc25A, 5 for Cdc25B, and 5 for Cdc25C. Splicing variants are particularly relevant for Cdc25B, since its most active isoform, Cdc25B2, is the only one detected in primary fibroblasts, while at least 3 different variants of splicing are present in immortalized fibroblasts.

The activity of these phosphatases is highly regulated during normal division of cells and in response to the activation of checkpoints, in order to assure a correct functioning of CDC/cyclin activity.

Considering all the mentioned issues, is not surprising to find Cdc25B reported in various types of cancer, suggesting its participation in pathogenesis and progression of malignant transformation of cells. It is known that Cdc25B is over expressed in 72% of pancreatic cancer cases, and together with gastric cancer, are the only 2 types of cancer which only over express Cdc25B exclusively, and no other isoform of this phosphatase.

In particular, pancreatic cancer is the fifth cause of death in many western countries, being one of the most aggressive and with the worst prognosis: a survival rate for 5 years of only 5%. Currently, the only treatment is surgery, but only 10% of the patients suffering from such a form of cancer are suitable candidates, while the remaining 90% has only an average of 4 to 5 months of survival time.

Considering only the 10% of patients which can receive a surgical treatment, less than 10% shows a survival rate higher than 5 years.

Currently, gemcitabine is the chemotherapeutic agent of first line to treat pancreatic cancer. Nevertheless, even when applying this agent, the survival is only 1 year in average. Thus, new strategies and ways of treatment need to be developed, being gene-therapy one interesting and promising option.

Up to date, nearly 66% of clinical trials of gene-therapy are directed to treat cancer. Among the key issues addressed by these therapies, are: increasing antitumor activity of immune cells by using genes coding cytokines, increasing the immunogenicity of the tumor by application of tumor antigens, using a "suicidal" gene which grants increased sensibility to certain pharmaceutical compounds. Other strategies include the blocking of oncogenes by using antisense genes, using tumor suppressor genes (p53), transfection of genes with antiangiogenic effect, using genes to increase resistance to certain pharmaceutical compounds to decrease toxicity of chemotherapy, and use of oncolytic viruses.

Among the oncolytic viruses, the two most used systems are retroviruses and adenoviruses, and adenoviruses are the system of choice given a safety issue, since adenoviruses are not oncogenic.

There are 51 human serotypes of adenoviruses, which are divided in 6 species, A to F. These are double strand linear DNA, with 35-36 kb length, contained in a protein capsid, which is formed by 240 hexagonal capsomers (hexons) covering the faces and edges, comprising the most abundant component, and 12 pentagonal (pentones) located in the vertices, from which extensions or fibers emerge.

Pentons and fibers are responsible of the interaction cell-virion. The fiber comprise a globular domain (knob) which serves as the main binding site "Coxsakie and adenovirus receptor" CAR, while the penton comprises a RGD domain (Arg-Gly-Asp), which interacts with the cell surface integrins, thus producing the endocytosis of the virion via clatrin vesicles.

The first generation of adenoviral vectors was able to infect tumoral cells, but unable to replicate, since E1A gene, responsible for replication, was deleted from its genome. Unfortunately, non-replicant viruses were found to be ineffective in achieving a proper therapeutic response. Thus, a new generation of conditionally replicative adenoviruses (CRAds) was created.

Two types of CRAds can be distinguished, one with a mutation or deletion of E1A or E1B gene, and the other where E1 genes are under transcriptional control of a tumor specific promoter (TSP). The replicated viruses can infect neighboring cells causing lysis, which will continue as long as the tumor specific promoter is active. Thus, CRAds are not only a carrier for gene transfer, but also an active therapeutic agent.

Currently, in China, there is an oncolytic adenovirus, (H101, Shangai Sunway Biotech), which combined with fluorouracil (5FU) and cisplatin has been accepted as a standard treatment for refractory nasopharyngeal cancer.

In terms of pancreatic cancer, this is the one with the highest number of mutations, compared to all other tumors. Genetic and epigenetic alterations have been reported, including mutations in protooncogene K-Ras and suppressor genes such as p53, Smad4/DPC4 and p16/CDKN2A. These alterations result in an uncontrolled progression of the cell cycle, with high resistance to cell arrest and apoptosis. Furthermore, there is an over expression of growth factors and its receptors in a significant amount of these tumors.

It is also known that expression levels of Cdc25B are increased in pancreatic cancer, but not in chronic pancreatitis or normal pancreas. In contrast, Cdc25A and Cdc25C do not show difference among normal samples and tumoral samples. Furthermore, in normal tissue, Cdc25B is expressed in 8% of cells, while in tumoral tissue the level of expression is 48%. Of the tumoral cells, Cdc25B is found in the nucleus as well as in cytoplasm.

Thus, Cdc25B is a good candidate to be used as promoter to direct the expression of adenoviral replication in tumoral cells.

A further requirement to have a proper adenovirus therapy for cancer is having efficient gene transfer. Thus, an important issue is the high variability of the expression receptor CAR in tumoral cells.

Many studies show that pancreatic cancer cells have a low expression of CAR; therefore diverse approaches need to be considered to modify or reduce this deficiency, including genetic modifications altering the capsid or using redirecting complexes, and also reducing directing to hepatocytes, which present high expression of CAR.

One approach is to modify the structure of the fiber of the adenovirus, substituting the binding protein to the receptor CAR (knob/fiber) with one of a different serotype, thus producing chimera adenoviruses, significantly improving the adenovirus infectivity.

Modification of the HI loop in the knob region of the fiber, with RGD-4C motifs has shown an increased infectivity of cells expressing low levels of CAR, compared to a native Ad5 fiber. This improvement could be explained by the interaction of integrins, usually over expressed in tumoral cells, with the modified fiber. It has also been shown that replacing the knob domain in Ad5, whose primary receptor is CAR, with an Ad3 knob domain, whose primary receptor are CD46, CD80, and CD86, increases the infectivity of cells showing a low expression of CAR.

US patent U.S. Pat. No. 6,033,856 discloses the promoter of cdc25B gene, a process to find these promoters and method of use in pharmaceutical compositions. The document describes murine sequences, and mentions that the sequences can be human, but the human Cdc25B sequence is not disclosed.

WO2010097419 describes an adenovirus with conditional replication wherein E1A expression is controlled by the promoter of the urokinase plasminogen activator (uPAR) or a fragment thereof. It is also mentioned that this adenovirus can be used in the preparation of a medicine for the treatment of cancer, in particular pancreatic cancer. Nevertheless, this document does not mention nor suggest using the promoter of the Cdc25B gene to produce a new oncolytic adenovirus.

WO0067576 describes a serotype 5 adenovirus with an increased infectivity and conditional replication, wherein these characteristics are the product of a modification in the knob domain of the fiber. It is also mentioned that the early genes are conditionally controlled, thus offering replication limited to specific cell types. Nevertheless, this document does not mention nor suggest an oncolytic adenovirus comprising the Cdc25B promoter, or the modification of the knob domain as described in the present invention.

US2010233125 discloses a serotype 5 adenovirus, whose fiber has been replaced with the fiber of serotype 3 adenovirus, and E1A and E1B are regulated by exogenous transcriptional regions. The adenovirus described is cytotoxic or oncolytic and can be used in the treatment of tumors. A process for its preparation and a medicine is also disclosed. Nevertheless, this document does not mention the use of a promoter sequence, such as Cdc25B, as disclosed in the present invention.

US20100297072 describes a pharmaceutical kit, comprising an oncolytic virus, and an immunostimulant drug. The document further describes a treatment method, but it does not describe an orthotopic cancer model, nor does it suggest the combination of an oncolytic adenovirus comprising a Cdc25B promoter combined with a chemotherapeutic agent.

US20010044420 describes the combination of gene therapy based on p53 gene and gemcitabine. Different cell lines are evaluated in terms of decrease in proliferation, but as will be seen in this application, the doses used for the viral vector are higher than the ones considered in the present invention, as well as the promoter considered to direct the replication of the virus.

US20090317456 describes a combination of gene therapy and an antiangiogenic agent. There is no description of an adenovirus similar to the description found in the present invention, wherein the oncolytic virus is specifically designed to target cancer combined with a chemotherapeutic agent.

US20070281041 describes a combination of MDA-7 which can be delivered by a virus, and a EGFR inhibitor, wherein the combination for cancer treatment can further comprise an anticancer drug, nevertheless, there is no mention nor suggestion for the treatment or use of the combination of an oncolytic adenovirus and a chemotherapeutic agent to treat a cancer characterized by Cdc25B over expression.

None of the documents found in literature report an oncolytic adenovirus, which is directed to cancer, characterized by an over expression of Cdc25B, and which combined with a chemotherapeutic agent, such as gemcitabine, produces a synergistic effect in the reduction of tumor size.

SUMMARY OF THE INVENTION

The purpose of this invention is to provide a pharmaceutical kit comprising an oncolytic virus, more preferably the oncolytic virus is an adenovirus. The kit also comprising a suitable chemotherapeutic agent. In a preferred embodiment, the pharmaceutical kit can be used in the treatment of hyperproliferative mammalian cells, such as, neoplastic cells. In a more preferred embodiment, the invention also provides a method for the treatment of cancer, wherein the cancers to be treated include, but are not limited to, ovarian cancer, pancreatic cancer, gastric cancer, a non-small cell lung cancer, small cell lung cancer, primary peritoneal cancer, hepatocarcinoma, melanoma, retinoblastoma, breast tumor, colorectal carcinoma, leukemia, lymphoma, brain tumor, cervical carcinoma, sarcoma, prostate tumor, bladder tumor, tumor of the reticuloendothelial tissues, Wilm's tumor, astrocytoma, glioblastoma, neuroblastoma, ovarian carcinoma, osteosarcoma, renal cancer, or head and neck cancer. In a preferred embodiment, the pharmaceutical kit is directed to the treatment of cancer characterized by the over expression of Cdc25B.

BRIEF DESCRIPTION OF THE FIGURES

FIG. 1. Human Cdc25B promoter scheme, 458 bp (The box shows the sequence corresponding to a 241 by fragment. In grey, the region with higher homology to murine promoter, comprising two SP1 boxes (SEQ ID NO: 22), a NF-Y box (SEQ ID NO: 23) and TATA box (SEQ ID NO: 24).

FIG. 4(a). Cytophatic effect in vitro. Pancreatic tumoral cell line BXPC3 infected with AdWT, Ad-5/3-WT, AV25CDCs 5/3, AV25CDC 5/3 and AV25CDCs, using MOIs between 1 to 1000 and cultured over 6 days until CPE determination. Cell viability was determined using MTT assay.

FIG. 4(b). Cytophatic effect in vitro. Pancreatic tumoral cell line HS766T infected with AdWT, Ad-5/3-WT, AV25CDCs 5/3, AV25CDC 5/3 and AV25CDCs, using MOIs between 1 to 1000 and cultured over 6 days until CPE determination. Cell viability was determined using MTT assay.

FIG. 4(c). Cytophatic effect in vitro. Pancreatic tumoral cell line Mia Paca 2 infected with AdWT, Ad-5/3-WT, AV25CDCs 5/3, AV25CDC 5/3 and AV25CDCs, using MOIs between 1 to 1000 and cultured over 6 days until CPE determination. Cell viability was determined using MTT assay.

FIG. 4(d). Cytophatic effect in vitro. Pancreatic tumoral cell line SW1990 infected with AdWT, Ad-5/3-WT, AV25CDCs 5/3, AV25CDC 5/3 and AV25CDCs, using MOIs between 1 to 1000 and cultured over 6 days until CPE determination. Cell viability was determined using MTT assay.

FIG. 5. (a) Cytophatic effect in vitro. Colon tumoral cell line HT29 was infected with AdWT, Ad-5/3-WT, AV25CDCs 5/3 AV25CDC 5/3 and AV25CDCs at MOIs between 1 to 1000 and cultured for 6 days until ECP determination. Cell viability was determined using MTT assay.

FIG. 5. (b) Cytophatic effect in vitro. Colon tumoral cell line LoVo was infected with AdWT, Ad-5/3-WT, AV25CDCs 5/3 AV25CDC 5/3 and AV25CDCs at MOIs between 1 to 1000 and cultured for 6 days until ECP determination. Cell viability was determined using MTT assay.

FIG. 6. (a) Cytophatic effect in vitro. Human fibroblasts (CCD1140Sk) infected with AdWT, Ad-5/3-WT, AV25CDCs 5/3, AV25CDC 5/3 and AV25CDCs at MOIs between 1 to 1000 and cultured for 6 days until ECP determination. Cell viability was determined using MTT assay.

FIG. 6. (b) Cytophatic effect in vitro. Human fibroblasts (HFL1) infected with AdWT, Ad-5/3-WT, AV25CDCs 5/3, AV25CDC 5/3 and AV25CDCs at MOIs between 1 to 1000 and cultured for 6 days until ECP determination. Cell viability was determined using MTT assay.

FIG. 6. (c) Cytophatic effect in vitro. Human fibroblasts (WI38) infected with AdWT, Ad-5/3-WT, AV25CDCs 5/3, AV25CDC 5/3 and AV25CDCs at MOIs between 1 to 1000 and cultured for 6 days until ECP determination. Cell viability was determined using MIT assay.

FIG. 6. (d) Cytophatic effect in vitro. Human keratinocytes (HACAT), infected with AdWT, Ad-5/3-WT, AV25CDCs 5/3, AV25CDC 5/3 and AV25CDCs at MOIs between 1 to 1000 and cultured for 6 days until ECP determination. Cell viability was determined using MTT assay.

FIG. 9: (A) In vivo effect of AV25CDC 5/3. SW1990 cells were injected subcutaneously to athymic mice N:NIH(S)–nu. AV25CDC 5/3 was IT administered when tumors reached an approximate volume of 100 mm$^3$ (1×10 viral particles/tumor). PBS was used as vehicle. Tumors were measured with a caliper. Animals were sacrificed when the approximate volume of the tumors reached 2500 mm3. Data is expressed as average ± SD. (B). Representative pictures of animals treated with A: PBS; B: GEM+PBS; C: AV25CDC 5/3; D and E: AV25CDC 5/3 +GEM.

FIG. 11: (A) In vivo effect in orthotopic tumors. AV25CDC 5/3 and AV25CDC 5/3 in combination with gemcitabine. SW1990 mcherry-Luc cells were injected orthotopically in the pancreas of athymic mice N:NIH(S)–nu. AV25CDC 5/3 was IT administered at 15 days post injection of tumoral cells (1×10$^9$ viral particles/tumor) and gemcitabine (15 mg/kg) was administered 24 hours after virus injection, three times during one week via intraperitoneal. PBS was used as vehicle. (B) Representative pictures of animals with orthotopic tumors of SW1990 mcherry Luc treated with: A: PBS; B: GEM+PBS; C: AV25CDC 5/3; D: AV25CDC 5/3 +GEM. (C) Macroscopic images of the tumors shown in (B).

DETAILED DESCRIPTION OF THE INVENTION

Figure 2:
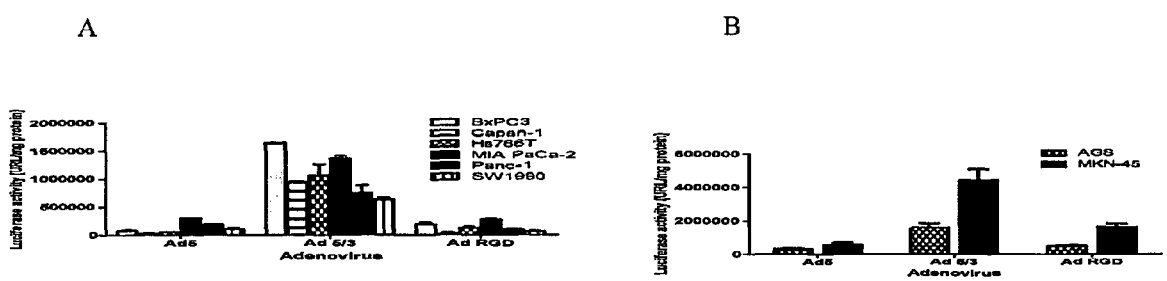
FIG. 2. Infectivity of vectors with capsid modifications in pancreatic (A) and gastric (B) tumoral cell FIG. 3. Measure of transcriptional activity of the Cdc25B fragments in pancreatic tumoral cell lines.

The present invention, a pharmaceutical kit, comprises:
An oncolytic adenovirus.
A suitable chemotherapeutic agent.
In a preferred embodiment the oncolytic adenovirus comprises a DNA sequence wherein three regions are essential for the present invention:
Binding region, for the recognition of target cells and infection thereof;
Tissue specific promoter directing the preferential expression and replication of the virus in target tissues;
Insulator sequence, blocking interaction with other non-desired enhancer sequences.

In a preferred embodiment, the adenovirus is a serotype 5 adenovirus. In a more preferred embodiment the adenovirus is a chimeric adenovirus, and the binding region from a serotype 5 adenovirus is replaced with the binding region of a serotype 3 adenovirus.

In a preferred embodiment, the tissue specific promoter is the complete promoter of the human Cdc25B gene, with a sequence with at least 80% homology with said promoter. In a more preferred embodiment, the tissue specific promoter is a fragment of the human Cdc25B promoter, or a sequence with at least 80% homology to a fragment of the human Cdc25B promoter.

In a particular embodiment of the invention, the promoter fragment is the sequence described in SEQ ID NO: 1 or in SEQ ID NO:2, or a sequence with at least 80% homology to the sequence described in SEQ ID NO:1 or SEQ ID NO:2.

In a preferred embodiment, the insulator sequence is the one described in SEQ ID NO:3 or a sequence with at least 80% homology to SEQ ID NO:3.

In a further embodiment, the DNA sequence of the oncolytic adenovirus is SEQ ID NO: 4 or SEQ ID NO:5 or a sequence with at least 80% homology to SEQ ID NO: 4 or at least 80% homology to SEQ ID NO:5.

The chemotherapeutic agent of the pharmaceutical kit, is a chemotherapeutic agent selected from: ARA-C, aclarubicin, actinomycin, alemtuzumab, alitretinoin, altretamine, aminolevulinicacid, amsacrine, anagrelide, antiestrogen, antineoplastic, arsenictrioxide, asparaginase, azacitidine, 8-azaguanine, bevacizumab, bexarotene, bleomycin, bortezomib, bropirimine, busulfan, cabazitaxel, capecitabine, carboplatin, carboquone, carmofur, carmustine, catumaxomab, celecoxib, cetuximab, chemicallylinkedfab, chlorambucil, cisplatin, cladribine, clofarabine, crizotinib, cyclophosphamide, cytarabine, dacarbazine, dasatinib, daunorubicin, decitabine, demecolcine, denileukindiftitox, dhapaclitaxel, dichloroaceticacid, docetaxel, doxorubicin, edrecolomab, efaproxiral, epirubicin, epoxomicin, erlotinib, estramustine, etoglucid, etoposide, everolimus, ferruginol, fludarabine, fluorouracil, fotemustine, fulvestrant, gefitinib, gemcitabine, gemtuzumabozogamicin, glembatumumabvedotin, hydroxycarbamide, idarubicin, ifosfamide, imatinib, irinotecan, ixabepilone, lapatinib, lipoplatin, lomustine, lonidamine, mafosfamide, mannosulfan, masoprocol, mechlorethamine, melphalan, mercaptopurine, methotrexate, methylaminolevulinate, metoart, miltefosine, mitobronitol, mitoguazone, mitomycin, mitotane, mitoxantrone, monomethylauristatine, mubritinib, myocet, nafoxidine, nelarabine, nilotinib, nimustine, oblimersen, omacetaxinemepesuccinate, ortataxel, oxaliplatin, paclitaxel, panitumumab, pazopanib, pegaspargase, pelretin, pemetrexed, pentostatin, personalizedmedicine, picoplatin, pipobroman, pirarubicin, pixantrone, plicamycin, porfimersodium, prednimustine, procarbazine, psc833, raltitrexed, reditux, rituximab, romidepsin, satraplatin, semustine, sorafenib, sparsomycin, streptozotocin, sunitinib, talampanel, tamibarotene, taxane, taxoid, tegafur, temoporfin, temozolomide, temsirolimus, teniposide, tesetaxel, thiotepa, thymidylatesynthaseinhibitor, tiazofurin, tioguanine, toceranib, topotecan, trabectedin, trastuzumab, trastuzumabemtansine, treosulfan, tretinoin, triaziquone, trofosfamide, valrubicin, vascular-targetingagent, vinblastine, vincristine, vindesine, vinorelbine, vorinostat, zorubicin.

In a more preferred embodiment, the chemotherapeutic agent is gemcitabine.

The invention also provides a method of therapeutic treatment, wherein the adenovirus of the present invention is administered to a patient suffering from cancer, wherein the cancer is selected, but not limited to, from ovarian cancer, pancreatic cancer, gastric cancer, a non-small cell lung cancer, small cell lung cancer, primary peritoneal cancer, hepatocarcinoma, melanoma, retinoblastoma, breast tumor, colorectal carcinoma, leukemia, lymphoma, brain tumor, cervical carcinoma, sarcoma, prostate tumor, bladder tumor, tumor of the reticuloendothelial tissues, Wilm's tumor, astrocytoma, glioblastoma, neuroblastoma, ovarian carcinoma, osteosarcoma, renal cancer, or head and neck cancer.

In a more preferred embodiment, the cancer is characterized by an over expression of Cdc25B. In a particular embodiment, the adenovirus of the pharmaceutical kit of invention is administered using any method and route known in the art, such as for example systemically, regionally, or locally; by intra-arterial, intratumoral, intravenous (IV), parenteral, intra-pleural cavity, or local administration and intra-tumoral.

In a further embodiment, the dose of the virus is from 1 to 1010 viral particles per tumor.

A chemotherapeutic agent is administered to the patient at 72 hours. In a particular embodiment, gemcitabine is the chemotherapeutic agent, and gemcitabine is applied using any method and route known in the art, such as for example systemically, by intra-arterial, intravenous (IV).

Gemcitabine should be administered intravenously at a dose of 1000 mg/m$^2$ over 30 minutes on Days 1 and 8 of each 21-day cycle (Human use).

WORKING EXAMPLES OF THE INVENTION

Cell Lines

Human pancreatic carcinoma and adenocarcinoma cell lines BxPC-3 (ATCC# CRL-1687), Capan-1 (ATCC# HTB-79), Hs766T (ATCC# HTB-134), MIA PaCa-2 (ATCC# CRL-1420), PANC-1 (ATCC# CRL-1469) SW1990 (ATCC# CRL-2172) were grown in recommended medium, supplemented with 10% Fetal Bovine Serum (FBS), 2.5 U/ml penicillin, and 2.5 µg/ml streptomycin. Human colon carcinoma cell lines LoVo (ATCC# CCL-229) and HT29 (ATCC# HTBL-38) were grown in DMEM:F12 1:1 medium, supplemented with 10% FBS, 2.5 U/ml penicillin, and 2.5 µg/ml streptomycin. Embryonic lung fibroblast cell lines WI-38 (ATCC# CCL-75) and HFL-1 (ATCC# CCL-153) and normal human skin fibroblast cell line CCD 1140 Sk (ATCC# CRL 2714), were grown in high glucose DMEM medium (4.5 g/l glucose) supplemented with 10% FBS. Embryonic kidney cells HEK 293 (ATCC# CRL 1573) were grown in high glucose DMEM medium (4.5 g/l glucose) supplemented with 10% FBS. Gastric carcinoma cell lines AGS, MKN-45, were grown in RPMI 1640, supplemented with 10% FBS, 2.5 U/ml penicillin, and 2.5 µg/ml streptomycin. All cell lines were maintained at 37° C. and a controlled atmosphere with 5% $CO_2$.

Plasmids

The promoters considered in the present invention were cloned in pGL3-Basic vector (Promega Corp., Madison, Wis.). This vector has the modified Firefly luciferase gene (luc+) to avoid binding to genetic regulatory factors, deleting restriction sites, avoiding protein transport to peroxysomes and the presence of a Kozak sequence in 5' terminal of the luciferase gene optimizing transduction efficiency. Also, the promoters were cloned in pShuttle-1 plasmid (pAdeasy adenoviral System). When small scale preparations were considered (1-5 ml), plasmids were purified using alkaline lysis method. For medium scale (10-100 ml) preparations, which were used subsequently in digestion reactions using restriction enzymes for further ligations, the Plasmid Midi kit (QIAGEN GmbH, Hilden, Germany) was used.

PCR products were cloned in pGEM-T easy vector (Promega Corp., Madison, Wis., USA), and then subcloned to the required plasmids.

Polymerase Chain Reaction (PCR)

PCR reactions were performed using Minicycler (MJ Research Inc., Whaltam, Mass.) or PTC-200 (MJ Research Inc., Whaltam, Mass.) thermocyclers. Since human Cdc25B promoter has not been described, suitable primers were designed based on the sequence of murine Cdc25B promoter. These primers are detailed in Table 1, which helped to amplify two fragments of the putative human promoter of 241 pb and 458 pb.

TABLE 1

Oligonucleotides used for PCR and sequencing

| Primer | Purpose | Sequence (5'-3') | T (° C.) | |
|---|---|---|---|---|
| Cdc25B pas-Hind III | PCR Cdc25B Promoter | GCGAAGCTTCGCCGGGCTCAGGCACCAGCCA | 62 | SEQ ID NO: 6 |
| Cdc25B pas-BglII | PCR Cdc25B Promoter | GAGATCTCGCCGGGCTCAGGCACCAGCCA | 62 | SEQ ID NO: 7 |
| Cdc25B ps-Xho I | PCR Cdc25B Promoter | GGCTCGAGGGGATAAATCTTAATTCCTCCG | 62 | SEQ ID NO: 8 |
| Cdc25B-MluI | PCR Cdc25B Promoter | CGACGCGGTGTCTAACGCAGACCGTACAGCCC | 62 | SEQ ID NO: 9 |
| pShuttle F | Sequencing | GAAGTGAAATCTGAATAATTTTGTG | 52 | SEQ ID NO: 10 |
| pShuttle R | Sequencing | CAAAACTACATAAGACCCCCAC | 52 | SEQ ID NO: 11 |
| P3 | Sequencing | CTAGCAAAATAGGCTGTCCCC | 52 | SEQ ID NO: 12 |
| P2 | Sequencing | CTTTATGTTTTGGCGTCTTCCA | 55 | SEQ ID NO: 13 |
| SP6 | Sequencing | GATTTAGGTGACACTATAG | 50 | SEQ ID NO: 14 |
| T7 | Sequencing | TAATACGACCACTATAGGG | 53 | SEQ ID NO: 15 |
| ACTINA B S | Real Time PCR B Actin | AGA AAA TCTGGCACCACACC | 60 | SEQ ID NO: 16 |
| ACTINA B AS | Real Time PCR B Actin | CAGAGGCGTACAGGGATAGC | 60 | SEQ ID NO: 17 |
| Cdc25B S | Real Time PCR Cdc25B | GGGCAAGTTCAGCAACATCGTGGA | 60 | SEQ ID NO: 18 |
| Cdc25B AS | Real Time PCR Cdc25B | GTAGCCGCCTTTCAGGATATACAT | 60 | SEQ ID NO: 19 |
| E4S | Real Time PCR E4 | ACAAGCTCCTCCCGCGTTAG | 60 | SEQ ID NO: 20 |
| E4 AS | Real Time PCR E4 | ACTACGTCCGGCGTTCCAT | 60 | SEQ ID NO: 21 |

The amplification cycle consisted in an initial denaturation step at 95° C. for 5 minutes, followed by 35 amplification cycles: 94° C., 1 minute, annealing step (variable, depending on each product, specified in Table 1) 1 minute, and 72° C. for 1 minute, followed by a final extension at 72° C. for 10 minutes.

Restriction Enzymes Digestion

All digestion reactions were performed in the conditions recommended by the manufacturer, during 3 to 16 hours. The result of the restriction was verified by electrophoresis separation in agarose gels (0.8-1.6%) in a TAE solution (40 M Tris-acetato, 2 mM $Na_2EDTA.2H_2O$, pH 8.5) with ethidium bromide (0.5 µg/µl) and visualized under UV trans-illuminator (Ultraviolet Products Inc., Upland, Calif.).

Purification and Quantitation of DNA Fragments

Purification of restriction products was performed in agarose gel electrophoresis and the fragment containing the DNA was cut for further purification using glass wool columns, or alternatively using Qiaex II kit (QIAGEN, GmbH, Hilden, Germany). For DNA fragment purification, used in ligation or plasmids, the quantitation was performed using a NanoDrop spectrophotometer (ND-1000, NanoDrop Technologies, Inc.)

Ligations

T4 bacteriophage ligase (New England Biolabs Inc., Beverly, Mass.) was used according to recommendation from the manufacturer. 1:1 to 3:1 insert:vector ratios were used, calculating the ratio between fragments following the next formula:

$$\left(\frac{\text{ng vector} \times \text{Kb insert}}{\text{Kb vector}}\right) \times \left(\frac{\text{insert}}{\text{vector}}\text{ratio}\right) = \text{ng insert}$$

At least 50 ng and at most 100 ng vector and 20 or 100 units of DNA ligase were used to ligate the cohesive or blunt ends, respectively, in a final volume from 10 µl to 20 µl. Samples were maintained at room temperature for 1 hour, and maintained at 4° C. until the bacterial transformation step.

Bacterial Transformation

Heat shock method, developed by Dagert et al, was used to transform bacteria.

DNA Sequencing

PCR amplified fragments were sequenced at the Sequencing Service at Fundación Instituto Leloir, using universal primers SP6 and T7, present in pGEM T and TOPO-pCR4 primers (Invitrogen Corp., Carlsbad, Calif.) flanking the cloned products, P2 and P3 primers to amplify pGL3 vector, or pShuttle sense and pShuttle antisense designed to sequence the inserts in pShuttle plasmid or adenoviral DNA (Table 1)

Luciferase Activity Assay

Cells were plated in 24-well plates with a density of $7\times10^4$ cells/well. After 24 hours, the following non replicative adenoviruses were used to infect the cells: AV-5/3Cdc25-241-Luciferase and AV-5/3-Cdc25-458 Luciferase. Each treatment was performed in triplicate and for each cell line, incubating non replicative adenovirus in 200 ul DMEM 2% FBS and after 2 hours, 800 ul of culture medium, corresponding to the culture medium of each cell line supplemented with FBS, was added. Cells were maintained for 46 hours in an incubator at 37° C. and 5% $CO_2$.

To perform the luciferase activity assay, the Dual Luciferase Reporter Assay System (Promega Corp., Madison, Wis.) kit was used. This system expresses simultaneously two individual reporter enzymes in the same system, allowing the evaluation of the activity produced by Firefly luciferase (*Photinus pyralis*) and Renilla (*Renilla reniformis*) in a sequential assay. The luminescent readings were determined with a Genios luminometer (TECAN, Maennedorf, Switzerland).

Data was normalized as described below:

$$\left(\frac{\text{Firefly luciferase units}}{\text{Renilla luciferase untis}}\right) = \text{Relative Luciferase Units } (RLU)$$

Real Time Quantitative PCT

In order to determine if Cdc25B promoter would be useful for the construction of a conditional oncolytic virus, Cdc25B mRNA levels were determined in different pancreatic tumoral cell lines, as well as in non-tumoral cell lines. Total RNA was obtained from each of the cell lines under study, using Trizol method (Invitrogen), according to manufacturer's instructions. Total RNA concentration was determined using NanoDrop (ND-1000 Spectrophotometer, NanoDrop Technologies, Inc.), while integrity was determined using a 1% agarose gel electrophoresis. SuperScript II (Invitrogen) kit was used to synthesize the first cDNA strand. RT-PCR used 5 µg of total RNA. 1 ul cDNA was used in a final amplification reaction volume of 25 ul, which contained 1 U Taq Platinum (Invitrogen) polymerase, 1×PCR Buffer (20 mmol/L Tris-Cl 8pH 8.4, 50 mol/L KCl, 1.5 mmol/L $Mg_2Cl$, 2.5 g bovine serum albumin, 0.4 umol/L of each specific primer, 200 umol/L triphosphate deoxinucleotides and 0.3× SYBR Green solution. Specific primers for Cdc25B and B Actin are detailed in Table 1. Determination of RT-PCR quantization was performed on iCycler iQ System (Bio-Rad Laboratories). PCR conditions were the following: 8 min 30 s at 95° C. and then 40 cycles of 45 s at 95° C., 30 s at 60° C., and 40 s at 72° C. All reactions were performed in triplicate. Data analysis was performed using iCycler software (BioRad Laboratories).

Viral Stock Production

Viruses were constructed using homologous recombination system in bacteria (Adeasy Adenoviral Vector System), wherein the gene of interest is subcloned first in a transference vector (pShuttle) and then transferred to the viral genome (pAdEasy-1) using homologous recombination in E. coli. Transfer vectors were linearized using PmeI and together with the vectors, with and without capsid modifications, BJ5183 bacteria were co transformed, where homologous recombination occurs in vivo. Colonies obtained in this way were checked using Hind III and Bgl II digestion. Clones presenting the expected pattern were recovered in DH5 α electromax bacteria, which were also checked using the restriction pattern to identify positive recombinant clones, and were subsequently sequencing. These clones were digested using PacI and transfected into 911 cells for virus production. Viruses were purified using cesium chloride gradients. Adenoviral preparations titration was made using DICT50 in HECK 293 cells, or based on optical density (O.D.).

Viral Replication

Viral replication was determined quantifying E4 gene (E4 Orf1), using Real Time Quantitative PCR ((MxPro3005P, Stratagene). PCR conditions were as follows: 150 s at 94° C. and then 39 cycles of 45 s at 94° C., 30 s at 60° C., and 30 s at 72° C. All reactions were performed in triplicate. Data analysis was performed using MxPro3005P software from Stratagene, comparing the samples to a standard. Standard curves were generated using serial dilutions of 1010 copies of retroviral DNA in a genomic DNA control solution.

Cytopathic Effect in a Monolayer, using MTT Assay

Cells were plated on 24-well plates ($10^4$ cells per well). Cells were infected at different Multiplicity of Infection (MOI) with WT Ad or AV25CDC. 6 days after infection, cell viability was determined using MTT (3-(4,5-cimethylthiazol-2-yl)-2,5-diphenyl terazolium bromide) assay.

In Vivo Assays

Subcutaneous Model

Athymic mice N:NIH(S)-nu from 8 to 10 weeks were used. Mice were inoculated subcutaneously in one of the flanks with 5×106 cells SW-1990 (pancreatic adenocarcinoma). When tumors reached in average to a volume of 100 $mm^3$, treatments were started. Mice were assigned randomly to 4 groups.

Group 1: received 3 intratumoral injections of the vehicle (PBS), once every 48 hours.

Group 2: received 3 intratumoral injections of AV25CDC 5/3, once every 48 hours.

Group 3: received intraperitoneal (IP) injection of Gemcitabine Sandoz S.A. (15 mg/kg) three times during one week.

Group 4: received 3 intratumoral injections of AV25CDC 5/3, once every 48 hours. After the last virus injection, gemcitabine (15mg/kg) was injected IP three times during one week.

Tumors were measured with caliper and the volume was estimated with the following formula:

$$[\text{length (mm)} \times \text{width (mm)}^2]/2$$

Animals were sacrificed when the tumor volumes reached 2500 $mm^3$. Values are expressed as average±SD.

Orthotopic Model

Athymic mice N:NIH(S)-nu from 8 to 10 weeks were used. The pancreatic cancer orthotopic modeling nude mice was performed according to the method described by Hotz, H. et. al (2003). Animals were anesthetized with IP injection of a mixture of ketamine (0.15 mg/g) and xylazine (0.015 mg/g). Afterwards, an abdomen incision was made exposing pancreas and spleen. 500,000 SW-1990 cells (pancreatic adenocarcinoma), resuspended in physiological saline solution (PBS) and a matrigel solution (total volume of 50 ul), were orthotopically injected in the tail of pancreas, finally the incision was closed. After 15 days of tumor establishment, treatments were started. Mice were assigned randomly in four groups. The following 2 experiments were performed.

Orthotopic Experiment 1

AV25CDC 5/3 virus administration or PBS administration was performed 15 days post establishment of the tumor Group 1: Intratumoral administration of PBS (50 ul)

Group 2: Intratumoral administration of virus (109 pv in 50 ul PBS)

Group 3: Intratumoral administration of virus (109 pv in 50 ul PBS), 24 hours after viral injection, gemcitabine (15mg/kg) was administered IP three times during one week Group 4: Intratumoral administration of PBS, 24 hours later, gemcitabine (15 mg/kg) was administered IP three times during one week.

Orthotopic Experiment 2

Equivalent to Experiment 1, but using stable pancreatic tumoral cells for mcherry Luc (generated by lentiviral infection) and administering two doses of AV25CDC 5/3 at 15 and 25 days post tumor establishment.

Tumor growth was evaluated by luciferase activity, IP injecting the substrate D-luciferin (32 mg/kg) and bioluminescence was measured using IVIS50 system Xenogen (software Living Image 2.20.1). 40 days after application of the first dose of virus, animals were sacrificed and the weight and volume of tumors was evaluated.

Statistical Analysis

All in vivo studies were subjected to analysis of variance (ANOVA) followed by a Test of Tukey.

Survival studies, for the subcutaneous model, were analyzed using the Kaplan-Meyer method, and compared with Log-Rank test.

Results

Cloning of two fragments of the human Cdc25B promoter in pGL3 and pShuttle promoters Since this promoter is not described in humans, the selected fragments were amplified with primers designed considering the murine promoter. These fragments correspond to sequences with homology between human Cdc25B gen and the murine promoter, including a putative transcription start site for the human gene, having no homology to the transcription start site described for murine. The higher homology between the selected fragments and the murine promoter is in the −110 to +4 region, with respect to the murine transcription start site, comprising the following consensus regions: TATA box, NFY site and two SP1 sites, which are described as functional in the murine promoter (FIG. 1). The amplified fragments of Cdc25B human gene start at region 3141 to 3590, for the bigger fragment and from 3144 to 3394 for the smaller fragment.

The fragments of the Cdc25B promoter were amplified using PCR from a human DNA sample using the primers described in Table 1. These PCR products were cloned in pGEM-T easy vector (Promega Corp., Madison, Wis., USA) obtaining the vectors: pGEM-Cdc25B 241p.b and pGEM-Cdc25B 458 p.b. The latter was sub cloned in the pGL3-Basic plasmid (Promega Corp., Madison, Wis., USA) upstream of the luciferase reporter gene. Thus, pGEM and pGL3 were digested with restriction enzymes XhoI and BglII in the case of the 241 pb fragment and MluI and HindIII in the case of the 458 pb fragment. Afterwards, and using the same restriction enzymes, the promoter fragments were subcloned in the vectors pShuttleIXPLuc and pShuttleIXPE1A, obtaining the following plasmids: pShuttle I Cdc25B 241 Luc, pShuttle I Cdc25B 241 E1A, pShuttle I Cdc25B 458 Luc, pShuttle I Cdc25B 241 E1A, which were used in the production of virus using the Adeasy Adenoviral Vector System, previously described.

All clones were checked using restriction enzymes digestion profiles and sequencing using universal primers SP6 and T7 for pGEM-Cdc25B 241 and pGEM-Cdc25B 458 and primers P3 and P2 for pGL3-Cdc25B 241 and pGL3-Cdc25B 458 and primers pShuttle F and pShuttle R.

Construction of Non Replicative Adenovirus using Universal Promoters and Modifications in the Capsid to Evaluate the Infectivity Level A series of non replicative adenovectors were constructed with and without modifications to the viral capsid. Specifically, the backbone fiber Ad5 (Adenovirus serotype 5) shown in Table 2, in order to better determine if the infectivity level is improved over the wild type virus. Evaluated modifications were: incorporating a RGD (Arg-Gly-Asp) motif in the knob domain of the fiber, which would interact with αv integrins of the cellular surface. Also, the modification involving the incorporation of a chimera fiber 5/3, i.e., replacing the Ad5 knob domain, whose primary cell receptor is the "coxsakie and adenovirus receptor" (CAR), for the Adenovirus serotype 3 (Ad3) knob domain, which binds to CD46, CD80 and CD86 receptors.

This allowed the evaluation of infectivity in vitro of several tumoral cell lines.

TABLE 2

Non replicative adenovirus with modifications in the viral capsid to evaluate infectivity level with different modifications Adeno 5 CMV Luc Ren
Adeno RGD CMV Luc Ren
Adeno 5/3 CMV Luc Ren
Adeno 5 SV40 Luc FireF
Adeno RGD SV40 Luc FireF
Adeno 5/3 SV40 Luc FireF Selection of Vector with the most Effective Viral Capsid Modification Adenovectors constructed with modifications in the viral capsid were tested in the following pancreatic tumoral cell lines: BxPC3, Capan-1, Hs766T, MIAPaCa-2, PANC-1, SW1990 and in gastric tumoral cell lines: AGS and MKN-45, in order to determine the level of infectivity of each of them.

The modification involves adding a chimeric fiber 5/3 which showed having the greater capacity to infect pancreatic as well as gastric tumoral cell lines (FIG. 2).

Measure of the promoter activity of two cloned sequences of human promoter Cdc25B for the construction of adenovirus In a first stage, messenger RNA (mRNA) produced levels were measured using real time quantitative PCR, in tumoral cell lines, as well as normal human cell lines (Table 3), using the following primers: Cdc25B S, Cdc25B AS, ACTINAB S and ACTINAB AS. Pancreatic tumoral cell lines (BXPc3, Hs766T, MiaPaCa-2, PANC-1 y SW-1990) express high levels of mRNA of Cdc25B (Table 2), as gastric tumoral cell lines (MKN-45) and colon tumoral cell lines (LoVo y HT29), while fibroblasts (WI-38, HFL-1 and CCD114oSk) express only basal levels of Cdc25B mRNA.

TABLE 3 mRNA expression of Cdc25B in different tumoral and normal cell lines. The expression is relative to the expression in Wi38.

Cdc25B mRNA expression

| Tumoral cell lines | | | | | | Non-tumoral cell lines | |
|---|---|---|---|---|---|---|---|
| Pancreatic | Level of expression | Gastric | Level of expression | Colon | Level of expression | non-tumoral | Level of expression |
| BxPC3(c) | 9.73 | MKN-45 | 10.8 | HT29 | 7.12 | CCd1140sk | 1.09 |
| BXPC3 (50%) | 6.13 | | | LoVo | 5.65 | HFL1 | 1.02 |
| Mia-PaCa-2 (c) | 6.49 | | | | | WI38 | 1.00 |
| Mia-PaCa-2 (50%) | 6.65 | | | | | | |

TABLE 3-continued mRNA expression of Cdc25B in different tumoral and normal cell lines.
The expression is relative to the expression in Wi38.
Cdc25B mRNA expression

| Tumoral cell lines | | | | | | Non-tumoral cell lines | |
|---|---|---|---|---|---|---|---|
| Pancreatic | Level of expression | Gastric | Level of expression | Colon | Level of expression | non-tumoral | Level of expression |
| SW1990 (c) | 4.09 | | | | | | |
| SW1990 (50%) | 5.40 | | | | | | |
| Hs766T | 7.63 | | | | | | |
| Panc-1 | 15.4 | | | | | | |

Two non replicative viruses were constructed in parallel, with a modification in the selected capsid, where the fragments of the promoters under study were upstream of the luciferase gene, generating the viruses: AV25CDCsLuc-5/3 and AV25CDC Luc-5/3. In this way, the promoter activity was evaluated, measuring the enzymatic activity with the Dual Luciferase Reporter Assay System (Promega Corp., Madison, Wis.).

Figure 3:
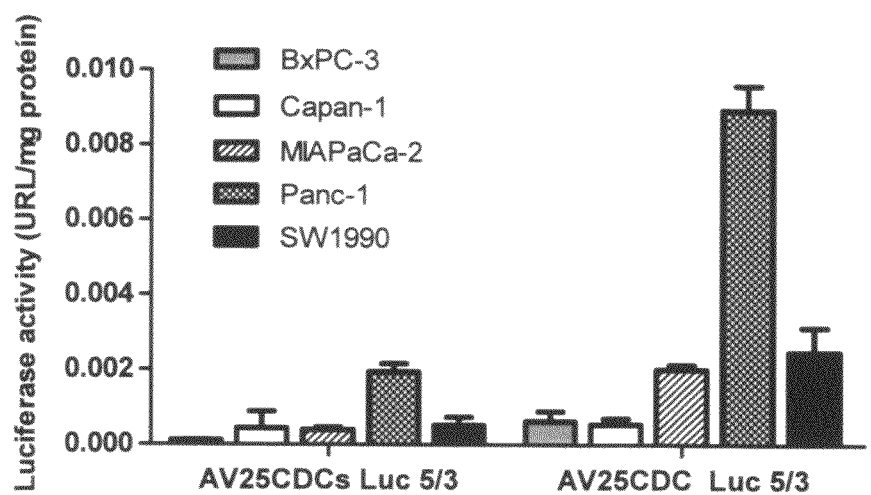

The results of three independent assays of activity are shown in FIG. 3. Cell lines BxPC-3, Capan-1, MIAPaCa-2, Panc-1 y SW1990 were used as model. As can be seen in FIG. 2, the 458bp promoter fragment Cdc25B shows the higher expression in almost all pancreatic tumoral cell lines, except in Capan-1. This higher transcriptional activity allowed selecting this promoter fragment to direct the expression of the viral gene E1A in an adenovector Construction of replicative adenovirus with Cdc25B promoters directing the expression of the viral gene E1A.

Using the homologous recombination system described previously, conditionally replicative viruses were constructed with a modification in the selected capsid: AV25CDCs 5/3 and AV25CDC 5/3, besides other virus without modifying the viral capsid AV25CDCs.

In Vitro Assays with AV25CDC Viruses a) Determination of cytopathic effect (CPE) in a monolayer In order to determine if adenovirus AV25CDCs 5/3, AV25CDC 5/3 and AV25CDCs were active and could replicate in cultured cells, different cell lines (pancreatic tumoral cell lines, gastric cell lines, colon cell lines, and normal fibroblast cell lines) were plated with wild type adenovirus 5 (AdWT) or type 5/3 wild type (Ad-5/3 WT), and with adenoviruses Adenovirus AV-5/3-Cdc25 241, AV25CDC 5/3 and AV25CDCs, with different multiplicities of infection (MOI).

It was observed that adenovirus with capsid modification had a higher cytopathic effect that the wild type capsid virus. Comparing both viruses with a modification in the capsid, AV25CDC 5/3 showed, in most of the cell lines tested, a cytopathic effect at a lower MOI than AV25CDCs 5/3. These results are coherent with the results shown in FIGS. 2 and 3, where a higher infectivity level is achieved by a modification in the capsid, and that the bigger promoter fragment has a higher transcriptional activity, both characteristics will allow the construction of a more effective virus (FIG. 4).

FIG. 5 shows that virus without capsid modification (AV25CDCs), showed a cytopathic effect in pancreatic cell lines with a 1000 MOI. In the case of colon cell lines HT29 and LoVo and gastric tumoral cell line, an effect is seen with MOI of 100, 1 and 10 respectively. While AV25CDC 5/3 produces a cytopathic effect at a MOI of 0.1, in pancreatic tumoral cell lines BxPC-3 y MIA PaCa-2, as well as in colon tumoral cell lines HT29 and LoVo and gastric tumoral cell line MKN-45. The pancreatic tumoral cell line SW-1990 showed a lytic effect at a MOI of 1.

In normal lung fibroblasts (WI-38 and HFL-1), and in normal skin fibroblasts (CCD1140 Sk), no lysis was observed with the non modified capsid. While the viruses with the modification, the attenuation effect in these lines was lower. In CCD1140 Sk, lysis was observed at MOI 1000 and in WI-38 and HFL-1, at MOI 10. Nevertheless, these MOIs are still one order of magnitude higher than the MOI at which lysis is produced in the case of all pancreatic tumoral cell lines (FIG. 6).

Based on the described results, the adenovirus with a modification in the capsid and the bigger fragment, AV25CDC 5/3 was selected to continue with in vivo studies.

b) Determination of viral replication of AV25CDC 5/3 in vitro

Figure 7:
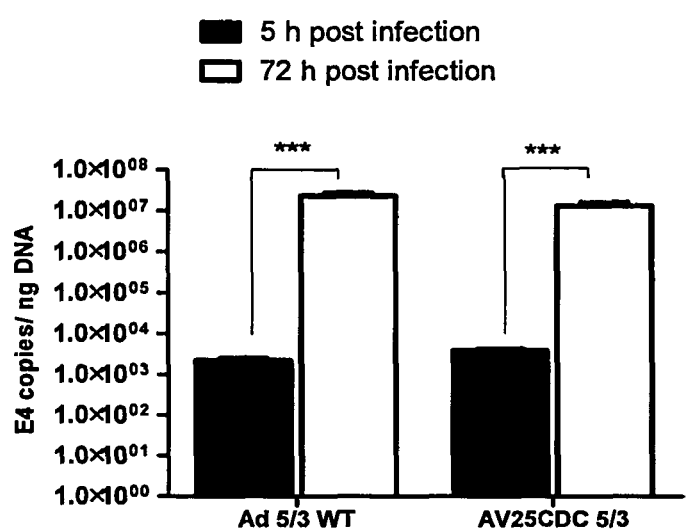
FIG. 7. Viral replication determination, measuring number of DNA copies of viral genomic E4 orf1 gene, at 5 hours and 72 hours post infection with AV25CDC 5/3 and Ad-5/3-WT viruses in SW1990 pancreatic tumoral cell lines.

Pancreatic tumoral cell lines (SW1990) were plated and infected with wild type 5/3 virus (Ad-5/3 WT), and with AV25CDC 5/3. Using real time quantitative PCR, viral replication was determined, measuring the number of copies of genomic viral DNA of E4 orf1 gene, at 5 and 72 hours post infection. The increase in the number of copies of the viral genome was determined in base to the number of copies found at 5 hours. At 72 hours, an increase in the number of copies of E4 is detected, 2 orders of magnitude, in the case of AV25CDC 5/3and three orders of magnitude in the case of Ad-5/3 WT. This increase shows the replicative activity of AV25CDC 5/3 (FIG. 7).

c) Determination of the combined effect of AV25CDC 5/3 and Gemcitabine

Figure 8:
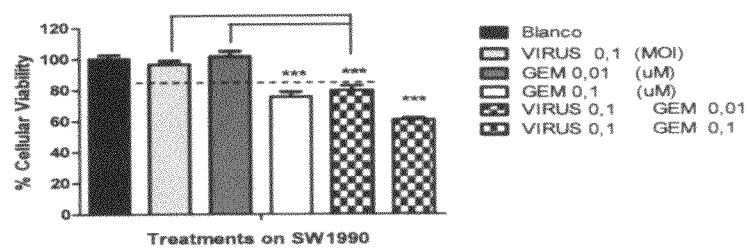
FIG. 8. In vitro synergic effect of AV25CDC 5/3 and gemcitabine in pancreatic tumoral cell line SW1990. Cells were infected with AV25CDC 5/3, at a MOI of 0.1 and 24 hours later gemcitabine was added at concentrations of 0.01 uM and 0.1 uM. Six days later, cell viability was measured using MTT assay.

Pancreatic tumoral cell lines (SW1990) were plated and infected with AV25CDC 5/3, at a MOI of 0.1 and 24 hours later, gemcitabine was added in concentrations of 0.01 uM and 0.1 uM. Six days later, cell viability was measured using MTT assay. There was no decrease on viability if only AV25CDC 5/3 is used at a MOI of 0.1, as well as no decrease was found adding gemcitabine at 0.01 uM. Nevertheless, the combination of both produced a decrease in cell viability of 20%. Using a higher concentration of gemcitabine, of 0.1 uM, on its own produced a decrease in viability of 20%, but combined with AV25CDC 5/3 at a MOI of 0.1, the viability decrease of 40%, considering the control (FIG. 8).

In Vivo AV25CDC 5/3 Assays a) Effect of AV25CDC 5/3 in subcutaneous tumors.

Figure 10:
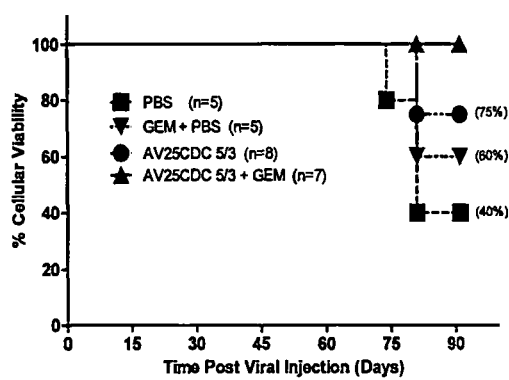
FIG. 10: Survival Kaplan-Meier plot after IT injection of AV25CDC 5/3 AV25CDC 5/3and PBS (vehicle) in SW1990 pancreatic tumoral cell line. Difference between treatments with AV25CDC 5/3 and PBS was statistically significant ($P<0.01$ on day 80).

To determine the oncolytic activity of AV25CDC 5/3 adenovirus in vivo, athymic mice N:NIH(S)-nu were used. Pancreatic tumoral cells (SW1990) were injected subcutaneously in mice of 30 grams approximately, which were daily controlled in order to evaluate tumor progression. When tumors reached an average volume of 100 $mm^3$, the treatments described before were applied. As shown in FIG. 9, treatment with intratumoral injection (IT) of AV25CDC 5/3, more gemcitabine, in tumoral cell lines SW1990, causing a significant decrease in tumoral volume at different days post injection, observing up to 90% decrease after 80 days. While the treatment with only IT injection with AV25CDC 5/3 caused a tumoral decrease of 55% compared to the tumors treated only with the vehicle. Survival of mice with tumoral cell line SW1990 treated with AV25CDC 5/3 and gemcitabine was significantly superior compared to the mice injected only with vehicle (p<0.01), (FIG. 10).

b) Effect of AV25CDC 5/3 in an orthotopic model of pancreas

Afterwards, an orthotopic model of pancreatic tumors was developed. Athymic mice were injected with SW1990 cells in the tail of pancreas. Two weeks post injection; the previously described treatments were applied. Two independent assays were performed. In assay 1, in the groups treated with the virus, only one IT injection with AV25CDC 5/3 was applied at day 40, where an average of $3.0 \times 10^{10}$ viral particles were found in the tumor indicating an active replication. On the other hand, biochemical parameters were evaluated at day 40, determining amylase, total and direct bilirubin, alkaline phosphatase (ALP) and aspartate aminotransferase (AST).

Tumoral marker levels Ca 19.9 were also determined.

Based on data shown in Table 4, biochemical parameters values are normalized in the cases treated with AV25CDC 5/3 and not in the case of treatment with only the vehicle (PBS), showing that the adenovirus is not only efficient in decreasing the size of the tumor, but also efficient in normalizing the biochemical parameters that were altered. A decrease in the levels of the tumoral marker Ca 19.9 was also observed in the case of treatment with AV25CDC 5/3 and combination with gemcitabine, which is interesting since the levels of this marker show an evolution similar to the therapeutic response of a malignant tumor.

TABLE 4

Biochemical profile in animals subjected to different treatments. The enzyme levels are expressed in Units/L (U/L), bilirubin values are expressed in mg/dL and tumoral marker Ca 19.9 levels are expressed in U/ml. Data is expressed as average ± SD and were determined at day 40 after injection of virus or PBS.

| Biochemical parameter | Treatments | | | | |
|---|---|---|---|---|---|
| | Naive | PBS | GEM | AV25CDC 5/3 | AV25CDC 5/3 + GEM |
| Ca 19.9 (*) | 10.2 | >50000 >50000 19010 | 27940 | 10055 >10000 17975 | 15905 20040 |
| Amylase | 769 ± 124 | 1242 ± 133 | 1151 ± 386 | 808.8 ± 170 | 680 ± 5.3 |
| Total Bilirubin | 0.76 ± 0.05 | 0.81 ± 0.05 | 0.78 ± 0.05 | 0.78 ± 0.02 | 0.8 ± 0.01 |
| Direct bilirubin | 0.18 ± 0.04 | 0.14 ± 0.01 | 0.14 ± 0.02 | 0.13 ± 0.01 | 0.12 ± 0.01 |
| ALP | 241.5 ± 61 | 157.8 ± 25 | 119.3 ± 25 | 134.2 ± 23 | 132.5 ± 29 |
| GOT (AST) | 212.5 ± 47 | 305 ± 137 | 280 ± 64 | 183 ± 37 | 183.8 ± 55 |
| GPT (ALT) | 48.3 ± 6.8 | 74.5 ± 26 | 47 ± 17 | 45.8 ± 14 | 39.8 ± 5 |

(*) In the case of Ca 19.9 marker, the number of samples was not equal for each treatment since in some cases, the volume of the sample was not enough to determine this parameter.

15 days after the tumor was established. While in assay 2, two IT injections with AV25CDC 5/3 were applied, at 15 days and 25 days after establishment of the tumor. Forty days after the first injection with AV25CDC 5/3 mice were sacrificed. Tumors were weighed and measured with caliper and the volume was estimated as described previously.

In the first orthotopic assay, statistically significant differences were observed, in weight as well as volume, comparing tumors treated with the vehicle (PBS), tumors treated with AV25CDC 5/3 or tumors treated with AV25CDC 5/3 and gemcitabine (p<0.001). There is also an statistically significant difference between the tumors treated only with gemcitabine and the group treated with AV25CDC 5/3 and gemcitabine (p<0.05) (FIG. 11a). FIGS. 11b and 11c show the macroscopic effect of the described treatments.

In the second orthotopic assay, statistically significant differences were observed in weight as well as volume, comparing the tumors treated with the vehicle.(PBS), and the tumors treated with AV25CDC 5/3 or tumors treated with AV25CDC 5/3 and gemcitabine (p<0.001; p<0.01).

Figure 12:
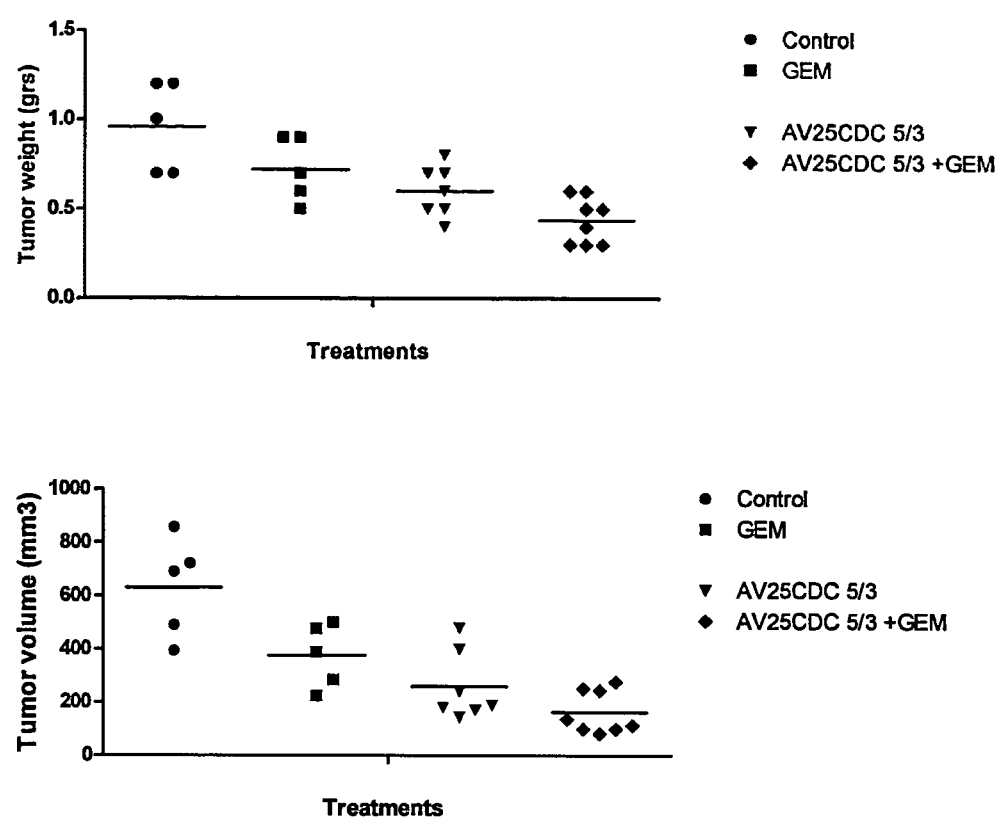
FIG. 12: In vivo effect of AV25CDC 5/3 in orthotopic tumors alone and in combination with gemcitabine. SW1990 cells were orthotopically injected in the pancreas of athymic mice N:NIH(S)–nu. AV25CDC 5/3 was IT administered at 15 and 25 days post injection of the cells (1×10$^9$ viral particles/tumor) and gemcitabine (15 mg/kg) was administered 24 hours after the first application of the virus, 3 times during one week. PBS was used as vehicle. Animals were sacrificed 40 days after the first administration of the virus.

There was no statistically significant difference between the tumors treated with only gemcitabine and the group treated with AV25CDC 5/3 and gemcitabine; nevertheless, a clear trend shows that the tumors are smaller in weight as well as volume (FIG. 12).

Also, to evaluate efficacy of AV25CDC 5/3, on orthotopic tumors caused by SW1990 cells, E4 expression was evaluated The present invention describes the development and characterization of a new oncolytic conditional replication adenovirus (CRAd) in pancreatic cancer. This new vector was named AV25CDC 5/3 and was constructed using a fragment of the promoter of the CDC25B gene to direct the expression of the viral gene E1A. AV25CDC 5/3 was very efficient inhibiting the growth of established pancreatic tumors in athymic mice, either subcutaneous or orthotopic. Also, it was highly effective in combination with gemcitabine.

There are different strategies for an oncolytic adenovirus to have a selective effect over tumoral cells and not over normal cells. One of them is based in modifications that can be performed to the capsid allowing directing of the adenovirus to target molecules in the surface of the tumoral cell or avoid directing adenovirus to normal cells, decreasing or minimizing toxic potential on, for example, liver.

An additional strategy involves deletion of viral genes required for replication of normal cells. Finally, transcriptional directing can be performed, where E1A is directed by tumor-specific promoters. In general, promoters selected for transcriptional directing correspond to genes over-expressed in tumoral tissue, compared to normal tissue. Thus, the majority of oncolytic viruses have been developed based on a promoter that can be active in more than one type of tumor, allowing a wide use in therapy not depending on the use of the adenovirus for only one type of cancer.

AV25CDC 5/3 was very selective as oncolytic virus over pancreatic tumoral cell lines, at very low MOI. In normal fibroblasts and normal keratinocytes showed cytophatic effects but at much higher MOIs than the required to produce lysis in pancreatic tumoral cells lines.

It is worth noting that AV25CDC 5/3 includes a sequence called "insulator" upstream of Cdc25B promoter, which is a 244 pair base fragment of the termination sequence of the bovine growth hormone, which blocks non-specific interference on the promoter and inhibits the action of neighboring regulatory elements present in the viral genome (ITR, encapsulation signal, etc.) Thus, the virus activity only depends on Cdc25B 458 promoter and allows the decrease or non-existence of non-specific activations.

In in vivo assays, AV25CDC 5/3 was used in orthotopic model with IT administration, where tumor growth inhibition was observed.

Using the orthotopic model is important since the representation of real patient situations is more accurate, since in this model, metastasis can occur, a process which is common in neoplasia and is not reproduced in subcutaneous tumors models, which in the vast majority are encapsulated and behave as a benign tumor.

Furthermore, no toxicity was observed in the liver of the animals treated with the vector, when autopsy analyses were performed. Also, the values for bilirubin, amylase and marker enzymes of hepatic functions were maintained in normal levels. This is very important, since hepatocytes are the major target of adenovirus circulating systemically.

AV25CDC 5/3 resulted efficient in therapy to inhibit ectopic and orthotopic tumors. In athymic mice, where no variation was observed in the levels of hepatic function and also, normalization of seric amylase, AST was observed, and a decrease in CA19.9 tumoral marker, indicating a therapeutic action of the adenovirus combined with gemcitabine.

The invention claimed is:

1. A pharmaceutical kit, comprising:
   a. an oncolytic adenovirus, comprising 3 regions:
      i. binding region;
      ii. promoter region;
      iii. insulator region;
   b. a chemotherapeutic agent;
      said oncolytic adenovirus DNA sequence is anyone of SEQ ID NOs 4 and 5, or a sequence with at least 80% homology to anyone of SEQ ID NOs: 4 and 5.

2. The pharmaceutical kit according to claim 1, wherein the adenovirus is a serotype 5 adenovirus.

3. The pharmaceutical kit according to claim 2, wherein the binding domain of the serotype 5 adenovirus has been replaced with the binding domain from a serotype 3 adenovirus.

4. The pharmaceutical kit according to claim 1, wherein the promoter region is the promoter of the human Cdc25B gene, or a sequence with at least 80% homology to SEQ ID NO: 1.

5. The pharmaceutical kit according to claim 4, wherein the promoter is a fragment of the human Cdc25B gene.

6. The pharmaceutical kit, according to claim 5, wherein the promoter sequence is SEQ ID NO: 1, or SEQ ID NO: 2 or a sequence with at least 80% homology to SEQ ID NO: 1, or at least 80% homology to SEQ ID NO: 2.

7. The pharmaceutical kit according to claim 1, wherein the insulator sequence is SEQ ID NO: 3 or a sequence with at least 80% homology to SEQ ID NO: 3.

8. The pharmaceutical kit according to claim 1, wherein the chemotherapeutic agent is selected from: ARA-C, aclarubicin, actinomycin, alemtuzumab, alitretinoin, altretamine, aminolevulinicacid, amsacrine, anagrelide, antiestrogen, antineoplastic, arsenictrioxide, asparaginase, azacitidine, 8-azaguanine, bevacizumab, bexarotene, bleomycin, bortezomib, bropirimine, busulfan, cabazitaxel, capecitabine, carboplatin, carboquone, carmofur, carmustine, catumaxomab, celecoxib, cetuximab, chemicallylinkedfab, chlorambucil, cisplatin, cladribine, clofarabine, crizotinib, cyclophosphamide, cytarabine, dacarbazine, dasatinib, daunorubicin, decitabine, demecolcine, denileukindiftitox, dha-paclitaxel, dichloroaceticacid, docetaxel, doxorubicin, edrecolomab, efaproxiral, epirubicin, epoxomicin, erlotinib, estramustine, etoglucid, etoposide, everolimus, ferruginol, fludarabine, fluorouracil, fotemustine, fulvestrant, gefitinib, gemcitabine, gemtuzumabozogamicin, glembatumumabvedotin, hydroxycarbamide, idarubicin, ifosfamide, imatinib, irinotecan, ixabepilone, lapatinib, lipoplatin, lomustine, lonidamine, mafosfamide, mannosulfan, masoprocol, mechlorethamine, melphalan, mercaptopurine, methotrexate, methylaminolevulinate, metoart, miltefosine, mitobronitol, mitoguazone, mitomycin, mitotane, mitoxantrone, monomethylauristatine, mubritinib, myocet, nafoxidine, nelarabine, nilotinib, nimustine, oblimersen, omacetaxinemepesuccinate, ortataxel, oxaliplatin, paclitaxel, panitumumab, pazopanib, pegaspargase, pelretin, pemetrexed, pentostatin, personalizedmedicine, picoplatin, pipobroman, pirarubicin, pixantrone, plicamycin, porfimersodium, prednimustine, procarbazine, psc833, raltitrexed, reditux, rituximab, romidepsin, satraplatin, semustine, sorafenib, sparsomycin, streptozotocin, sunitinib, talampanel, tamibarotene, taxane, taxoid, tegafur, temoporfin, temozolomide, temsirolimus, teniposide, tesetaxel, thiotepa, thymidylatesynthaseinhibitor, tiazofurin, tioguanine, toceranib, topotecan, trabectedin, trastuzumab, trastuzumabemtansine, treosulfan, tretinoin, triaziquone, trofosfamide, valrubicin, vascular-targetingagent, vinblastine, vincristine, vindesine, vinorelbine, vorinostat, zorubicin.

9. The pharmaceutical kit according to claim 1, wherein the chemotherapeutic agent is gemcitabine.

10. A method of treating cancer in a patient in need of such treatment, said treatment comprising administering the oncolytic adenovirus and a chemotherapeutic agent from the pharmaceutical kit described in claim 1.

11. The method of claim 10, wherein the cancer is selected from ovarian cancer, pancreatic cancer, gastric cancer, a non-small cell lung cancer, small cell lung cancer, primary peritoneal cancer, hepatocarcinoma, melanoma, retinoblastoma, breast tumor, colorectal carcinoma, leukemia, lymphoma, brain tumor, cervical carcinoma, sarcoma, prostate tumor, bladder tumor, tumor of the reticuloendothelial tissues, Wilm's tumor, astrocytoma, glioblastoma, neuroblastoma, ovarian carcinoma, osteosarcoma, renal cancer, or head and neck cancer.

12. The method of claim 10, wherein the cancer is characterized by an over expression of Cdc25B.

13. The method of claim 10, wherein the patient receives 1 to $10^{10}$ viral particles per tumor.

14. The method of claim 10, wherein the chemotherapeutic agent is administered 72 hours after administration of the oncolytic adenovirus.

15. The method of claim 10, wherein the chemotherapeutic agent is selected from: ARA-C, aclarubicin, actinomycin, alemtuzumab, alitretinoin, altretamine, aminolevulinicacid, amsacrine, anagrelide, antiestrogen, antineoplastic, arsenictrioxide, asparaginase, azacitidine, 8-azaguanine, bevacizumab, bexarotene, bleomycin, bortezomib, bropirimine, busulfan, cabazitaxel, capecitabine, carboplatin, carboquone, carmofur, carmustine, catumaxomab, celecoxib, cetuximab, chemicallylinkedfab, chlorambucil, cisplatin, cladribine, clofarabine, crizotinib, cyclophosphamide, cytarabine, dacarbazine, dasatinib, daunorubicin, decitabine, demecolcine, denileukindiftitox, dha-paclitaxel, dichloroaceticacid, docetaxel, doxorubicin, edrecolomab, efaproxiral, epirubicin, epoxomicin, erlotinib, estramustine, etoglucid, etoposide, everolimus, ferruginol, fludarabine, fluorouracil, fotemustine, fulvestrant, gefitinib, gemcitabine, gemtuzumabozogamicin, glembatumumabvedotin, hydroxycarbamide, idarubicin, ifosfamide, imatinib, irinotecan, ixabepilone, lapatinib, lipoplatin, lomustine, lonidamine, mafosfamide, mannosulfan, masoprocol, mechlorethamine, melphalan, mercaptopurine, methotrexate, methylaminolevulinate, metoart, miltefosine, mitobronitol, mitoguazone, mitomycin, mitotane, mitoxantrone, monomethylauristatine, mubritinib, myocet, nafoxidine, nelarabine, nilotinib, nimustine, oblimersen, omacetaxinemepesuccinate, ortataxel, oxaliplatin, paclitaxel, panitumumab, pazopanib, pegaspargase, pelretin, pemetrexed, pentostatin, personalizedmedicine, picoplatin, pipobroman, pirarubicin, pixantrone, plicamycin, porfimersodium, prednimustine, procarbazine, psc833, raltitrexed, reditux, rituximab, romidepsin, satraplatin, semustine, sorafenib, sparsomycin, streptozotocin, sunitinib, talampanel, tamibarotene, taxane, taxoid, tegafur, temoporfin, temozolomide, temsirolimus, teniposide, tesetaxel, thiotepa, thymidylatesynthaseinhibitor, tiazofurin, tioguanine, toceranib, topotecan, trabectedin, trastuzumab, trastuzumabemtansine, treosulfan, tretinoin, triaziquone, trofosfamide, vairubicin, vascular-targetingagent, vinblastine, vincristine, vindesine, vinorelbine, vorinostat, zorubicin.

16. The method of claim 10, wherein the chemotherapeutic agent is gemcitabine and is applied intravenously at a dose of 1000 mg/m$^2$ over 30 minutes on Days 1 and 8 of each 21-day cycle.

17. The method of claim 10 wherein the oncolytic adenovirus and the chemotherapeutic agent are administered systemically, regionally, or locally; by intra-arterial, intratumoral, intravenous (IV), parenteral, intra-pleural cavity, or local administration, as intra-tumoral.

* * * * *

SEQUENCE LISTING

```
<160> NUMBER OF SEQ ID NOS: 24

<210> SEQ ID NO 1
<211> LENGTH: 458
<212> TYPE: DNA
<213> ORGANISM: Homo sapiens

<400> SEQUENCE: 1
gccacgcgtg tgtctaacgc agaccgtaca gcccagctgg gtttagcaaa cttccgggag        60
ccagttggag cctctcccca tccctagcgg tgatcccagg tgacgacatg ccgcgggggg       120
tcctgcggag gccaccctag ggcgttgctg ctgcctttgg gagtgtggag ctccaaacca       180
tgtcgcgaga ggcggatttt gggaggccgg gatcctcgcg ccaggggat gtgcgagggt        240 gtgggataaa tcttaattcc tccggcccac ccaaagcctg gaaatccagc ctccgcgcct       300
cttgccctgc gggccccgcc ctcagtcccg ccctcatcta acccgctacc ccattggtgg       360
cgtccggcgg cgcggctgct gttattttc gaatatataa ggaggtggaa gtggcagctg       420
caactagagg cttccctggc tggtgcctga gcccggcc                             458

<210> SEQ ID NO 2
<211> LENGTH: 241
<212> TYPE: DNA
<213> ORGANISM: Homo sapiens

<400> SEQUENCE: 2
gccacgcgtg ctagcccggg ctcgagggat aaatctaatt cctccggccc acccaaagcc        60
tggaaatcca gcctccgcgc ctcttgccct gcgggccccg ccctcagtcc cgccctcatc       120
taacccgcta ccccattggt ggcgtccggc ggcgcggctg ctgttatttt tcgaatatat       180
aaggaggtgg aagtggcagc tgcaactaga ggcttccctg gctggtgcct gagcccggcg       240
a                                                                      241

<210> SEQ ID NO 3
<211> LENGTH: 244
<212> TYPE: DNA
<213> ORGANISM: Unknown
<220> FEATURE:
<223> OTHER INFORMATION: Sequence of the insulator

<400> SEQUENCE: 3
ctagtgctag agctcgctga tcagcctcga ctgtgcaaac tagttgccag ccatctgttg        60
tttgcccctc ccccgtgcct tccttgaccc tggaaggtgc cactcccact gtcctttcct       120
```

| aataaaatga ggaaattgca tcgcattgtc tgggtaggtg tcattctatt ctgggggtg | 180 |
|---|---|
| gggtggggca ggacagcaag ggggaggatt gggaagacaa tagcaggcat gctggggatg | 240 |
| gtac | 244 |

<210> SEQ ID NO 4
<211> LENGTH: 823
<212> TYPE: DNA
<213> ORGANISM: Unknown
<220> FEATURE:
<223> OTHER INFORMATION: Oncolytic adenovirus construction

<400> SEQUENCE: 4

| gcgcgtaata ctggtaccgc ggccgcctcg agtctagtgc tagtagctcg ctgatcagcc | 60 |
|---|---|
| tcgactgtgc aaactagttg ccagccatct gttgtttgcc cctcccccgt gccttccttg | 120 |
| accctggaag gtgccactcc cactgtcctt tcctaataaa atgaggaaat tgcatcgcat | 180 |
| tgtctgggta ggtgtcattc tattctgggg gtgggggtgg ggcaggacag caagggggag | 240 |
| gattgggaag acaatagcag gcatgctggg gatggtaccg gaggcctcgc tagccacgcg | 300 |
| tgtgtctaac gcagaccgta cagcccagct gggtttagca acttccggg agccagttgg | 360 |
| agcctctccc catccctagc ggtgatccca ggtgacgaca tgccgcgggg ggtcctgcgg | 420 |
| aggccaccct agggcgttgc tgctgccttt gggagtgtgg agctccaaac catgtcgcga | 480 |
| gaggcggatt ttggggaggcc gggatcctcg cgccaggggg atgtgcgagg gtgtgggata | 540 |
| aatcttaatt cctccggccc acccaaagcc tggaaatcca gcctccgcgc tcttgccct | 600 |
| gcgggccccg ccctcagtcc cgccctcatc taacccgcta ccccattggt ggcgtccggc | 660 |
| ggcgcggctg ctgttatttt tcgaatatat aaggaggtgg aagtggcagc tgcaactaga | 720 |
| ggcttccctg gctggtgcct gagcccggcg taagctcctc gctagccacg cgtggcggca | 780 |
| gatctccgga ctgaaaatga gacatattat tttgccacgg gag | 823 |

<210> SEQ ID NO 5
<211> LENGTH: 816
<212> TYPE: DNA
<213> ORGANISM: Unknown
<220> FEATURE:
<223> OTHER INFORMATION: Oncolytic adenovirus construction

<400> SEQUENCE: 5

| atctggtacc gcggccgcct cgagtctagt gctagagctc gctgatcagc ctcgactgtg | 60 |
|---|---|
| caaactagtt gccagccatc tgttgtttgc cctcccccg tgccttcctt gaccctggaa | 120 |
| ggtgccactc ccactgtcct ttcctaataa atgaggaaa ttgcatcgca ttgtctgggt | 180 |
| aggtgtcatt ctattctggg ggtgggggtg ggcaggaca gcaaggggga ggattgggaa | 240 |
| gacaatagca ggcatgctgg ggatggtacc ggaggcctcg ctagccacgc gtgctagccc | 300 |
| gggctcgagg gataaatcta attcctccgg cccacccaaa gcctggaaat ccagcctccg | 360 |
| cgcctcttgc cctgcgggcc ccgccctcag tcccgccctc atctaacccg ctaccccatt | 420 |
| ggtggcgtcc ggcggcgcgg ctgctgttat ttttcgaata taaggagg tggaagtggc | 480 |
| agctgcaact agaggcttcc ctggctggtg cctgagcccg gcgatagatc tgcgatctaa | 540 |
| gtaagctcct cgctagccac gcgtggcggc agatctccgg actgaaaatg agacatatta | 600 |
| tttgccacgg aggtgttatt accgaagaaa tggccgccag tcttttggac cagctgatcg | 660 |
| aagaggtact ggctgataat cttccacctc ctagccattt tgaaccacct acccttcacg | 720 |

-continued

```
aactgtatga ttttagacgt gacggccccc gaagatccca acgaggaggc ggttttcgca      780
gattttttcc ccgactctgt aatgttggca agtgcc                                816
```

<210> SEQ ID NO 6
<211> LENGTH: 31
<212> TYPE: DNA
<213> ORGANISM: Artificial Sequence
<220> FEATURE:
<223> OTHER INFORMATION: Primer

<400> SEQUENCE: 6

```
gcgaagcttc gccgggctca ggcaccagcc a                                      31
```

<210> SEQ ID NO 7
<211> LENGTH: 29
<212> TYPE: DNA
<213> ORGANISM: Artificial Sequence
<220> FEATURE:
<223> OTHER INFORMATION: Primer

<400> SEQUENCE: 7

```
gagatctcgc cgggctcagg caccagcca                                         29
```

<210> SEQ ID NO 8
<211> LENGTH: 30
<212> TYPE: DNA
<213> ORGANISM: Artificial Sequence
<220> FEATURE:
<223> OTHER INFORMATION: Primer

<400> SEQUENCE: 8

```
ggctcgaggg gataaatctt aattcctccg                                        30
```

<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9

```
cgacgcggtg tctaacgcag accgtacagc                                        30
```

<210> SEQ ID NO 10
<211> LENGTH: 25
<212> TYPE: DNA
<213> ORGANISM: Artificial Sequence
<220> FEATURE:
<223> OTHER INFORMATION: Primer

<400> SEQUENCE: 10

```
gaagtgaaat ctgaataatt ttgtg                                             25
```

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11

```
caaaactaca taagaccccc ac                                                22
```

<210> SEQ ID NO 12
<211> LENGTH: 21

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
ctagcaaaat aggctgtccc c                                        21

<210> SEQ ID NO 13
<211> LENGTH: 23
<212> TYPE: DNA
<213> ORGANISM: Artificial Sequence
<220> FEATURE:
<223> OTHER INFORMATION: Primer

<400> SEQUENCE: 13
ctttatgttt ttggcgtctt cca                                      23

<210> SEQ ID NO 14
<211> LENGTH: 19
<212> TYPE: DNA
<213> ORGANISM: Artificial Sequence
<220> FEATURE:
<223> OTHER INFORMATION: Primer

<400> SEQUENCE: 14
gatttaggtg acactatag                                           19

<210> SEQ ID NO 15
<211> LENGTH: 19
<212> TYPE: DNA
<213> ORGANISM: Artificial Sequence
<220> FEATURE:
<223> OTHER INFORMATION: Primer

<400> SEQUENCE: 15
taatacgacc actataggg                                           19

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
agaaaatctg gcaccacacc                                          20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
cagaggcgta cagggatagc                                          20

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18

| | |
|---|---|
| gggcaagttc agcaacatcg tgga | 24 |

<210> SEQ ID NO 19
<211> LENGTH: 24
<212> TYPE: DNA
<213> ORGANISM: Artificial Sequence
<220> FEATURE:
<223> OTHER INFORMATION: Primer

<400> SEQUENCE: 19

| | |
|---|---|
| gtagccgcct ttcaggatat acat | 24 |

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20

| | |
|---|---|
| acaagctcct cccgcgttag | 20 |

<210> SEQ ID NO 21
<211> LENGTH: 19
<212> TYPE: DNA
<213> ORGANISM: Artificial Sequence
<220> FEATURE:
<223> OTHER INFORMATION: Primer

<400> SEQUENCE: 21

| | |
|---|---|
| actacgtccg gcgttccat | 19 |

<210> SEQ ID NO 22
<211> LENGTH: 7
<212> TYPE: DNA
<213> ORGANISM: homo sapiens
<220> FEATURE:
<223> OTHER INFORMATION: SP1 box sequence

<400> SEQUENCE: 22

| | |
|---|---|
| cccgccc | 7 |

<210> SEQ ID NO 23
<211> LENGTH: 8
<212> TYPE: DNA
<213> ORGANISM: homo sapiens
<220> FEATURE:
<223> OTHER INFORMATION: NFY box sequence

<400> SEQUENCE: 23

| | |
|---|---|
| cccattgg | 8 |

<210> SEQ ID NO 24
<211> LENGTH: 7
<212> TYPE: DNA
<213> ORGANISM: homo sapiens
<220> FEATURE:
<223> OTHER INFORMATION: TATA box sequence

<400> SEQUENCE: 24

| | |
|---|---|
| tatataa | 7 |